(12) United States Patent
Cao et al.

(10) Patent No.: US 9,980,816 B2
(45) Date of Patent: May 29, 2018

(54) PROSTHETIC HEART VALVE, SYSTEM, AND METHOD

(71) Applicant: Edwards Lifesciences Corporation, Irvine, CA (US)

(72) Inventors: Hengchu Cao, Irvine, CA (US); Brian S. Conklin, Orange, CA (US); Paul A. Schmidt, Irvine, CA (US); Grace M. Kim, Seal Beach, CA (US); James A. Davidson, San Juan Capistrano, CA (US); Hoa T. Tran, Irvine, CA (US); Kristy L. Tam, Anaheim, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 314 days.

(21) Appl. No.: 14/663,101

(22) Filed: Mar. 19, 2015

(65) Prior Publication Data

US 2015/0230922 A1    Aug. 20, 2015

Related U.S. Application Data

(62) Division of application No. 13/104,648, filed on May 10, 2011, now Pat. No. 8,986,374.

(60) Provisional application No. 61/472,083, filed on Apr. 5, 2011, provisional application No. 61/332,885, filed on May 10, 2010.

(51) Int. Cl.
*A61F 2/24* (2006.01)

(52) U.S. Cl.
CPC .................. *A61F 2/2427* (2013.01)

(58) Field of Classification Search
CPC .................................. A61F 2/2427
See application file for complete search history.

(56) References Cited

U.S. PATENT DOCUMENTS

| | | | | |
|---|---|---|---|---|
| 5,861,028 A | * | 1/1999 | Angell | A61F 2/2412 623/2.11 |
| 5,984,973 A | * | 11/1999 | Girard | A61F 2/2418 623/2.38 |
| 6,558,418 B2 | * | 5/2003 | Carpentier | A61F 2/2412 623/2.14 |

(Continued)

FOREIGN PATENT DOCUMENTS

| | | |
|---|---|---|
| WO | 9528899 A1 | 11/1995 |
| WO | 98/43556 A1 | 10/1998 |

(Continued)

*Primary Examiner* — Son Dang
(74) *Attorney, Agent, or Firm* — Guy Cumberbatch; Pui Tong Ho

(57) ABSTRACT

Disclosed prosthetic valves can comprise a sewing ring configured to secure the valve to an implantation site. Some disclosed valves comprise a resiliently collapsible frame having a neutral configuration and a collapsed deployment configuration. Some disclosed frames can self-expand to the neutral configuration when released from the collapsed deployment configuration. Collapsing a disclosed valve can provide convenient access to the sewing ring, such as for securing the valve to the implantation site, as well as for the insertion of the valve through relatively small surgical incisions. Examples of delivery systems and methods for deploying the valves exhibit reduced patient trauma.

22 Claims, 17 Drawing Sheets

(56) References Cited

U.S. PATENT DOCUMENTS

| | | | | |
|---|---|---|---|---|
| 7,942,927 B2* | 5/2011 | Kaye | A61F 2/2445 623/2.11 |
| 8,052,750 B2* | 11/2011 | Tuval | A61F 2/2418 623/2.14 |
| 8,747,458 B2* | 6/2014 | Tuval | A61F 2/0095 623/1.11 |
| 9,248,016 B2* | 2/2016 | Oba | A61F 2/2418 |
| 2002/0133226 A1* | 9/2002 | Marquez | A61F 2/2412 623/2.11 |
| 2002/0161431 A1* | 10/2002 | Stobie | A61F 2/2427 623/2.11 |
| 2003/0050693 A1* | 3/2003 | Quijano | A61F 2/2445 623/2.11 |
| 2003/0125805 A1* | 7/2003 | Johnson | A61F 2/2412 623/2.11 |
| 2003/0167089 A1* | 9/2003 | Lane | A61F 2/2412 623/2.14 |
| 2003/0171805 A1* | 9/2003 | Berg | A61F 2/2412 623/2.14 |
| 2004/0024451 A1* | 2/2004 | Johnson | A61F 2/2412 623/2.11 |
| 2004/0127979 A1* | 7/2004 | Wilson | A61F 2/2418 623/2.1 |
| 2004/0148017 A1* | 7/2004 | Stobie | A61F 2/2427 623/2.11 |
| 2004/0186563 A1* | 9/2004 | Lobbi | A61F 2/2418 623/2.11 |
| 2006/0052867 A1* | 3/2006 | Revuelta | A61F 2/2418 623/2.18 |
| 2006/0241743 A1* | 10/2006 | Bergin | A61F 2/2409 623/2.11 |
| 2007/0050021 A1* | 3/2007 | Johnson | A61F 2/2418 623/2.14 |
| 2007/0162107 A1* | 7/2007 | Haug | A61F 2/2418 623/1.26 |
| 2007/0244551 A1* | 10/2007 | Stobie | A61F 2/2427 623/2.1 |
| 2007/0265701 A1* | 11/2007 | Gurskis | A61F 2/2409 623/2.1 |
| 2008/0033545 A1* | 2/2008 | Bergin | A61F 2/2427 623/2.11 |
| 2008/0071361 A1 | 3/2008 | Tuval et al. | |
| 2008/0071367 A1* | 3/2008 | Bergin | A61F 2/2427 623/2.11 |
| 2009/0076599 A1* | 3/2009 | Bergin | A61F 2/2427 623/2.11 |
| 2009/0259305 A1* | 10/2009 | Lane | A61F 2/2427 623/2.11 |
| 2011/0276128 A1* | 11/2011 | Cao | A61F 2/2409 623/2.11 |

FOREIGN PATENT DOCUMENTS

| | | |
|---|---|---|
| WO | 0224118 A1 | 3/2002 |
| WO | 2005072654 A1 | 8/2005 |
| WO | 2006127756 A2 | 11/2006 |

* cited by examiner

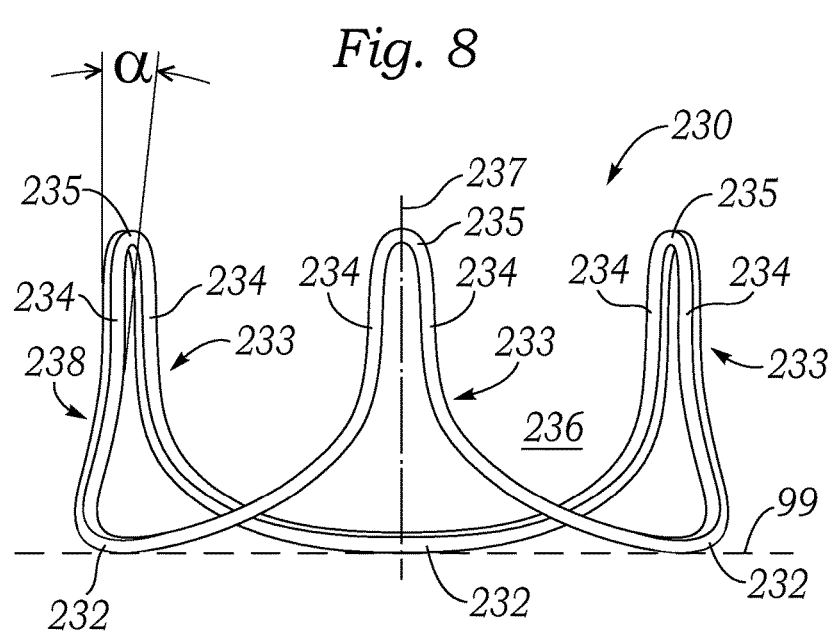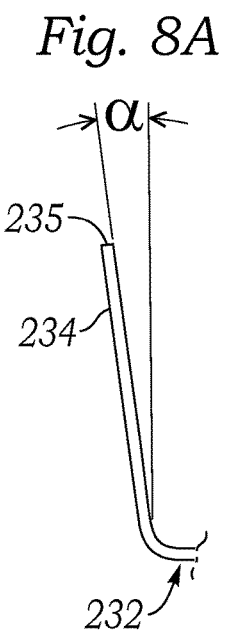
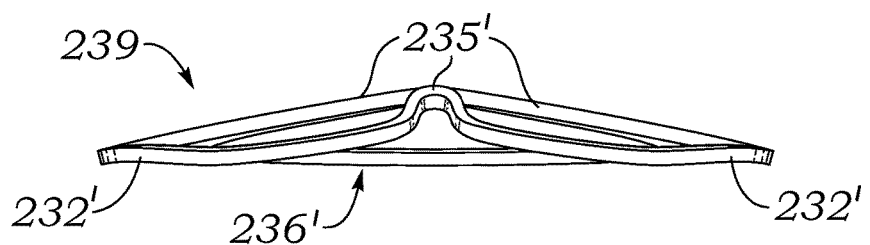
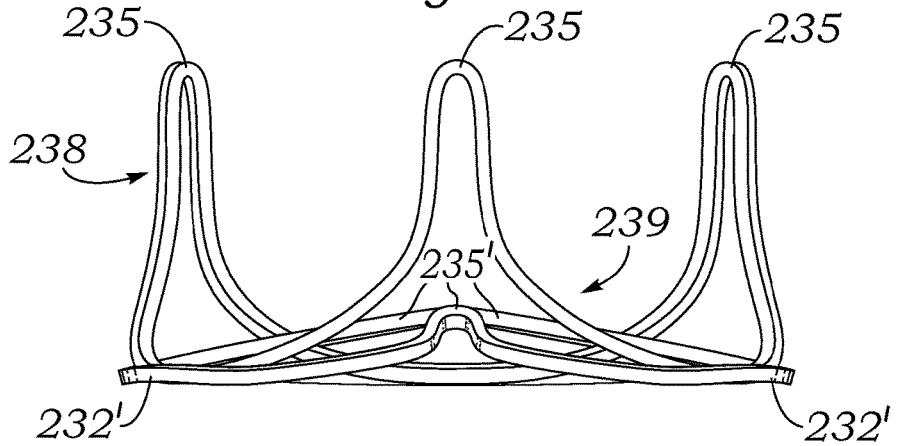

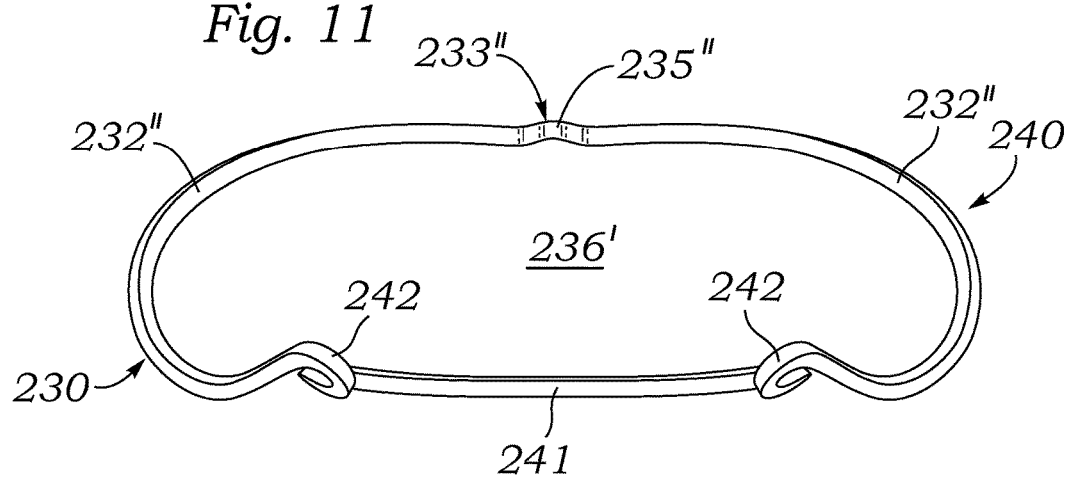
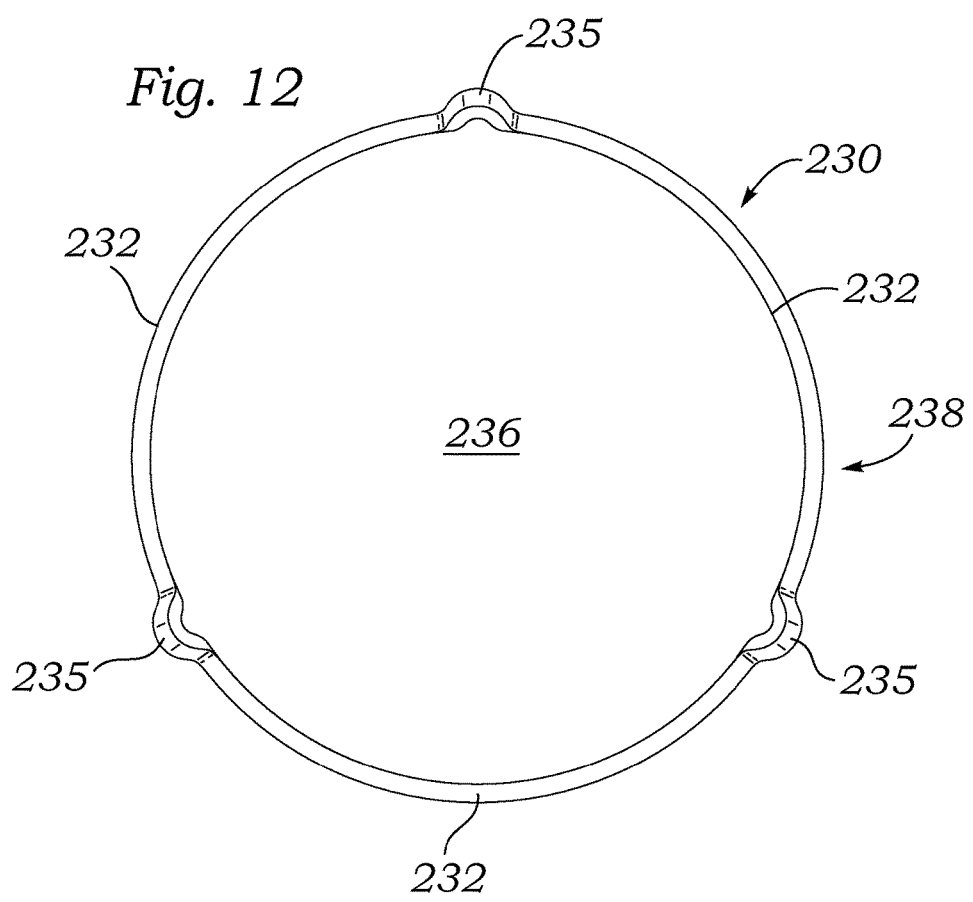

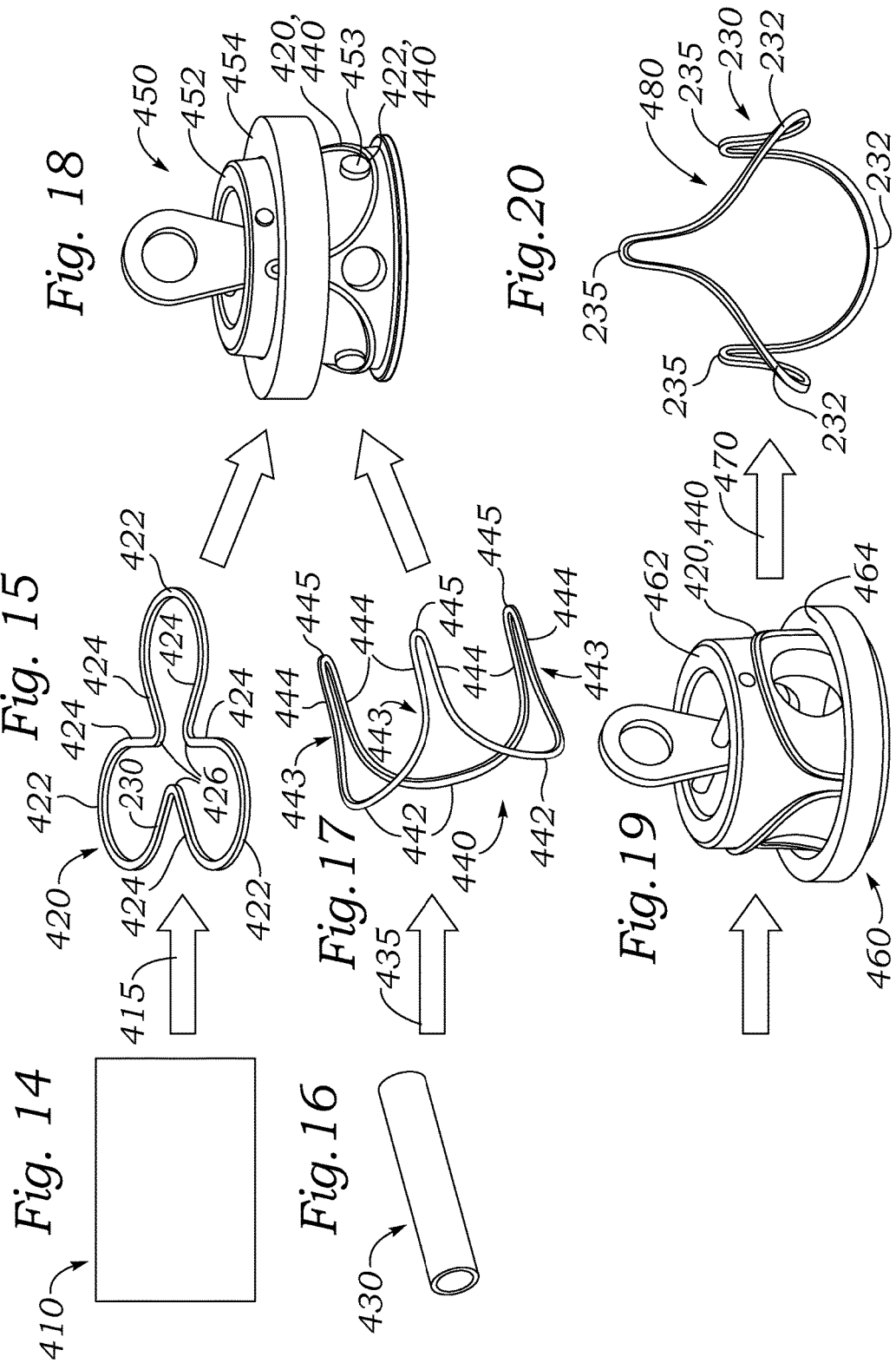

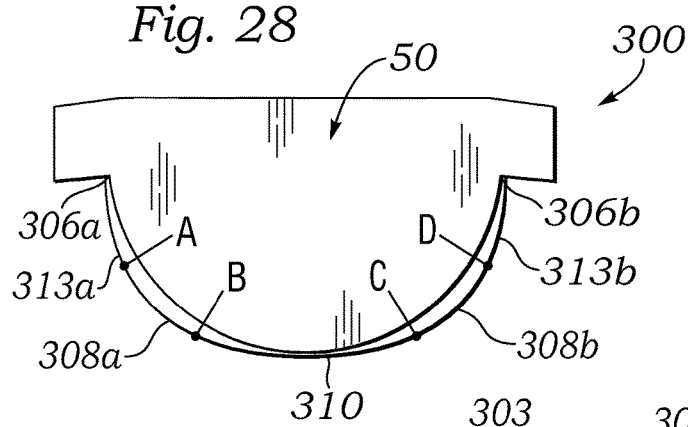
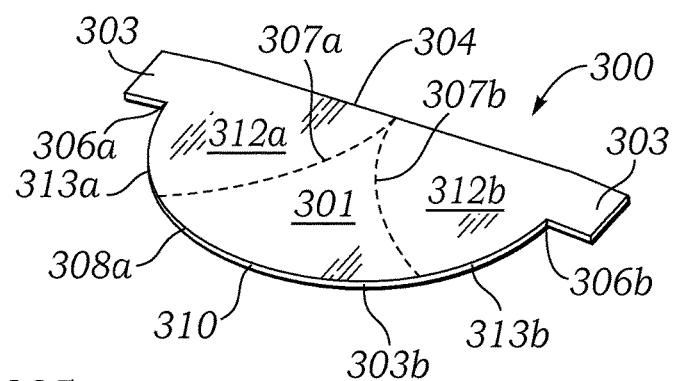
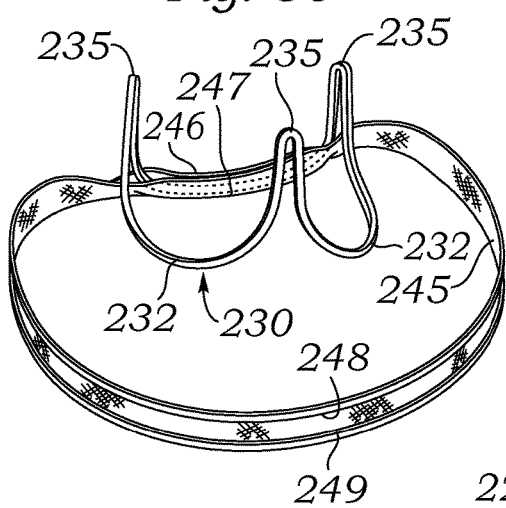
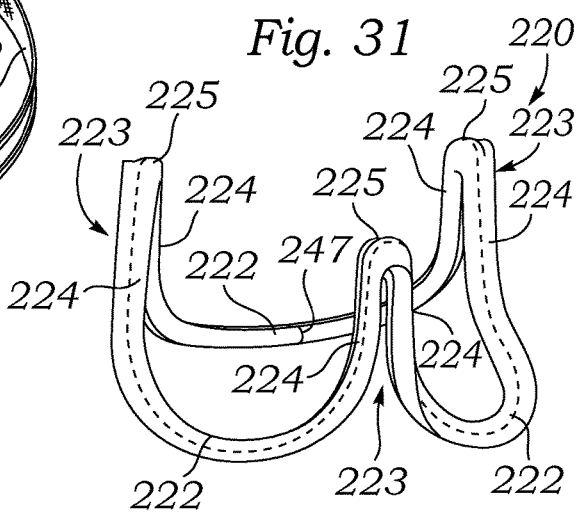

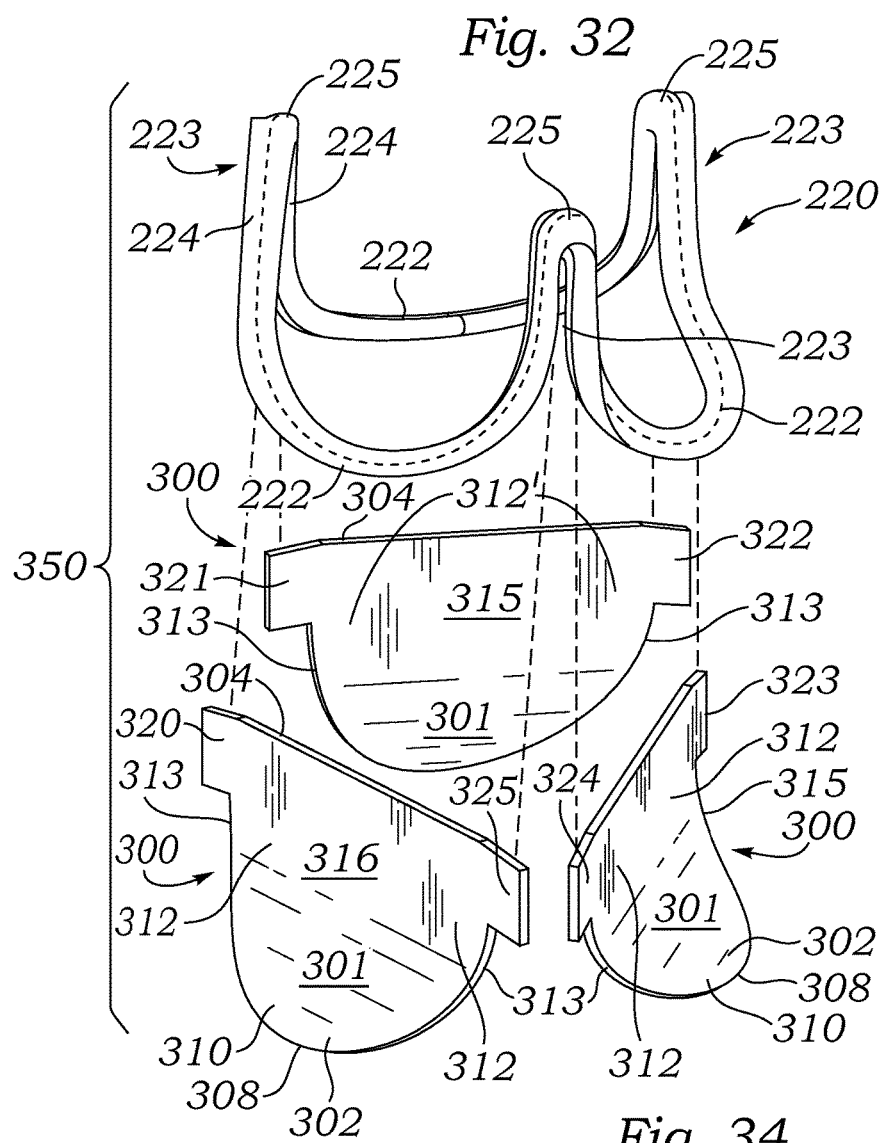
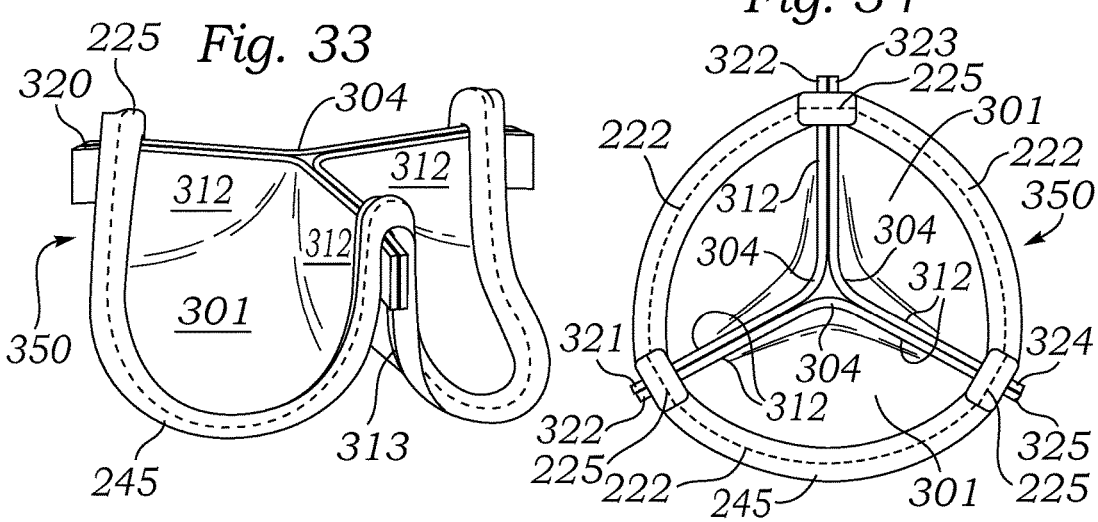

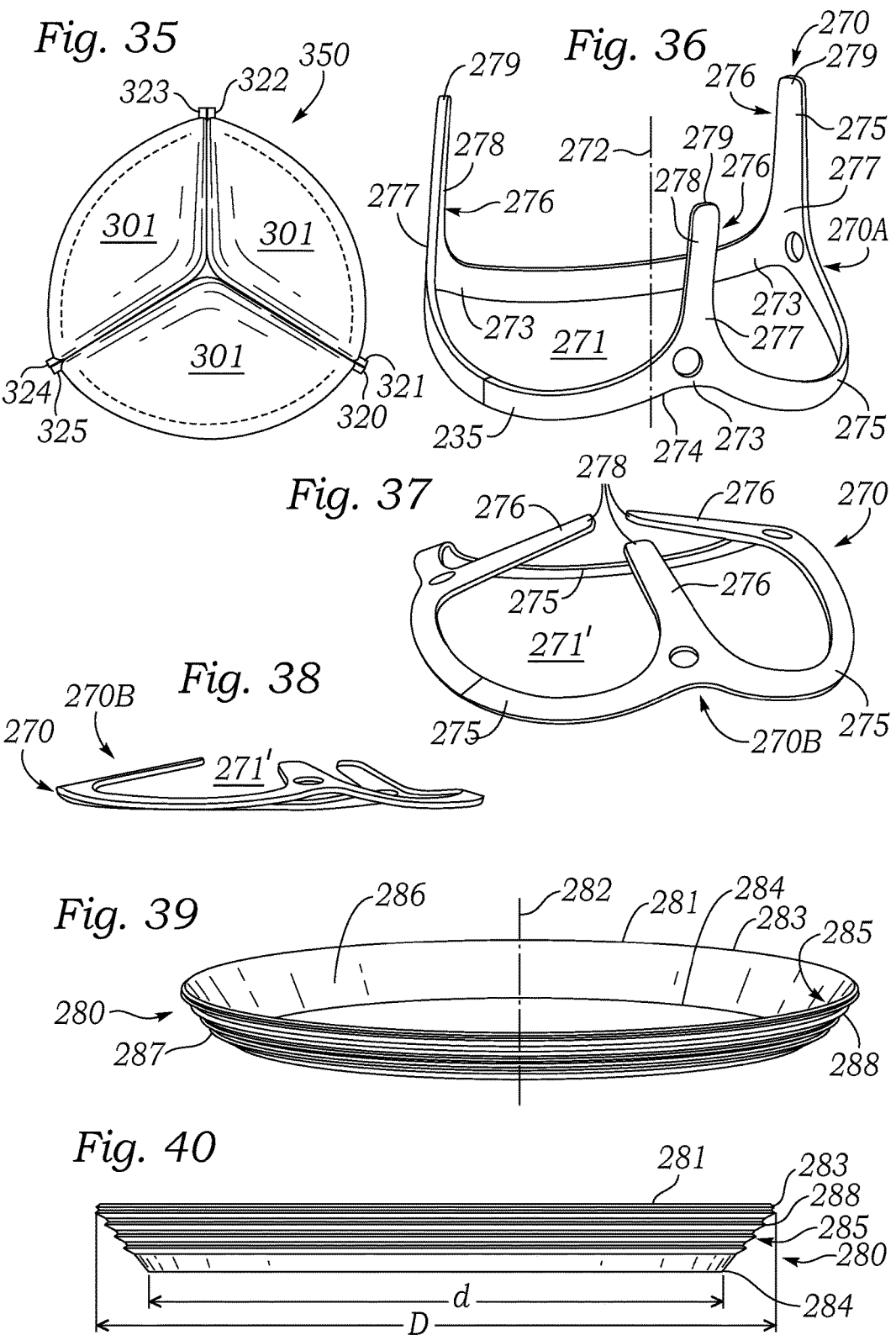

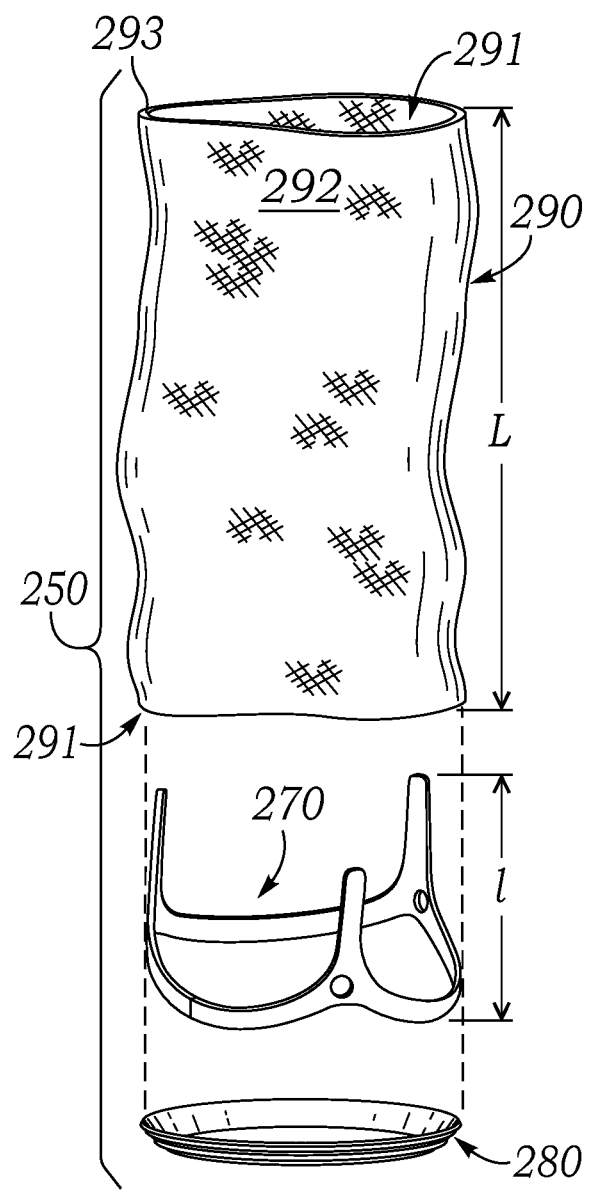

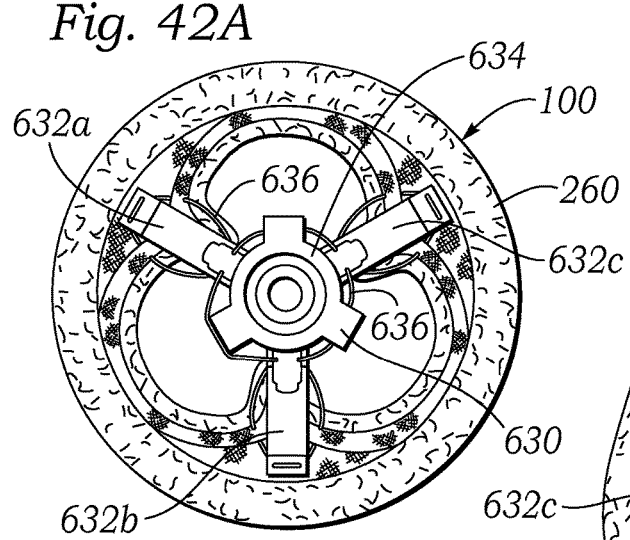
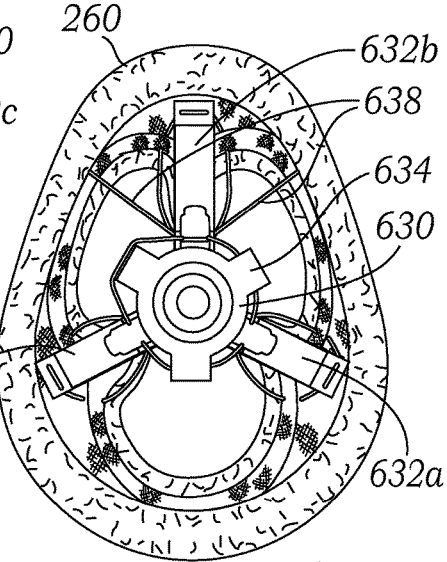
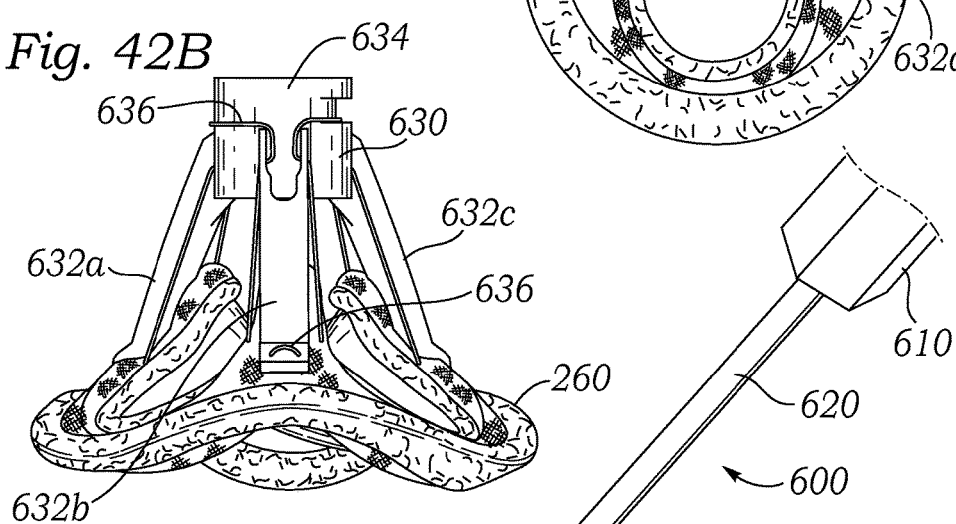
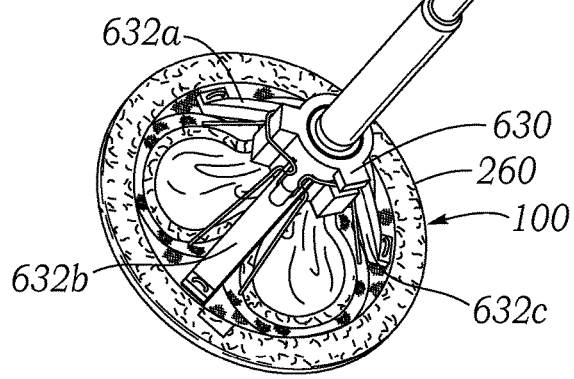

PROSTHETIC HEART VALVE, SYSTEM, AND METHOD

CROSS REFERENCE TO RELATED APPLICATIONS

This application is a divisional of U.S. patent application Ser. No. 13/104,648, filed May 10, 2011, now U.S. Pat. No. 8,986,374, which claims the benefit of U.S. Patent Application No. 61/332,885, filed May 10, 2010, and of U.S. Patent Application No. 61/472,083, filed Apr. 5, 2011, the disclosures of which are incorporated by reference in their entireties.

FIELD

The present application concerns implantable prosthetic valves and related methods and systems, such as for example, prosthetic aortic valves that can be implanted using minimally invasive surgical techniques.

BACKGROUND

In vertebrate animals, the heart is a hollow muscular organ having four pumping chambers as seen in FIG. 1: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atriums (see FIGS. 2, 3 and 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendineae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet coapt and form a seal, closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle. The remaining cardiac valves operate in a similar fashion.

Various surgical techniques may be used to repair a diseased or damaged valve. In a valve replacement operation, the damaged leaflets are typically excised and the annulus sculpted to receive a prosthetic valve. Due to aortic stenosis and other heart valve diseases, thousands of patients undergo surgery each year wherein the defective native heart valve is replaced by a prosthetic valve (either bioprosthetic or mechanical). Another, less drastic, method for treating defective valves is through repair or reconstruction, which is typically used on minimally calcified valves. One problem with surgical therapy is the significant insult it imposes on chronically ill patients and the associated high morbidity and mortality rates associated with surgical repair.

When a valve is replaced, surgical implantation of the prosthetic valve has typically required an open-chest surgery, during which the heart is stopped and the patient is placed on cardiopulmonary bypass (a so-called "heart-lung machine"). In one common surgical procedure, the diseased native valve leaflets are excised and a prosthetic valve is sutured to the surrounding tissue of the valve annulus. Because of the trauma associated with the procedure and the attendant duration of extracorporeal blood circulation, mortality rates during surgery or shortly thereafter typically have been high. It is well established that risks to patients increase with the duration of extracorporeal circulation. Due to such risks, a substantial number of patients with defective valves are deemed inoperable because their condition is too frail to withstand the procedure. By some estimates, up to about 50% of patients suffering from aortic stenosis and who are older than 80 years cannot undergo surgery for aortic valve replacement using conventional open-chest surgery.

Because of drawbacks associated with conventional open-heart surgery, percutaneous and minimally-invasive surgical approaches are garnering intense attention. Minimally invasive surgical techniques have been and continue to be developed. In successfully performed minimally invasive techniques, a conventional sternotomy can be avoided. Access to the heart can be by way of upper sternotomy or thoracotomy allowing a smaller incision and typically shorter healing times, as well as less pain for the patient. Blood loss is typically lower with minimally invasive techniques, hospital stays are shorter, and there may be lower morbidity and mortality rates as compared to conventional surgical techniques.

To obtain at least some of the potential benefits of the smaller incisions required by minimally invasive surgical techniques, prosthetic valves compatible with such techniques are needed. For instance, U.S. Pat. No. 5,411,522 to Andersen et al. describes a collapsible valve percutaneously introduced in a compressed state through a catheter and expanded in the desired position by balloon inflation.

Although such remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are widely accepted. Additionally, the long-term durability of remotely implanted devices is unknown.

In another approach, a flexible heart valve especially suitable for implanting in the aortic annulus has been proposed in U.S. Pat. No. 6,558,418 to Carpentier, et al., and U.S. Pat. No. 6,376,845 to Marquez, et al. More particularly, Carpentier and Marquez disclose single and multi-element frame-and-stent assemblies that include flexible cusps between adjacent commissure portions extending therefrom. A suture-permeable connecting band attached to the disclosed prosthetic valve follows the shape of (i.e., is coextensive with) the underlying frame. In the Carpentier and Marquez approach, the valve is secured by attaching the connecting band (and thereby, the entire contour of the underlying frame, including the cusp and commissure portions) to the surrounding natural tissue. Although this approach represents an advancement of surgically implantable valves, the commissure portions of the frame remain fixedly attached to, and cannot move independently of, the tissue since the sewing band is coextensive with the undulating frame. In addition, suturing the complex, undulating periphery of the sewing band can be difficult and time consuming, as various parts of the valve can interfere with access to the sewing band. Although the valves disclosed in the '418 and '845 patents could be collapsed and inserted through a small incision, such as a thoracotomy, it would be difficult to suture them to the native annulus through such a small incision due to the configuration of the sewing band.

Accordingly, there remains a need for an improved prosthetic heart valve that facilitates placement through small incisions, facilitates easier suture tying at the implantation site, and provides improved hemodynamics. In addition, devices for, and associated methods of, implanting such improved prosthetic valves in a body lumen are also needed, especially a more efficient procedure that reduces the duration a patient needs extracorporeal circulation to undergo a cardiac valve replacement.

SUMMARY

The present disclosure concerns embodiments of a prosthetic valve, delivery devices for the valve and methods for implanting the valve. The valve can be implanted at any of the native valve annuluses of the heart or within any other body lumen that requires a valve to regulate the flow of liquid (e.g., a vein). The valve in particular embodiments has a resiliently flexible, self-expandable frame that supports a fluid-occluding member, such as a leaflet structure comprising a plurality of leaflets. The valve frame desirably has flexible commissure posts that support the commissures of the leaflets. The valve frame can be placed in a collapsed delivery configuration to facilitate insertion of the valve into the body and attachment (e.g., by suturing) of the valve to a native annulus, such as the native aortic annulus. For example, the valve frame can allow the valve to be radially collapsed so that the valve can be more easily inserted through a surgical incision made in a body lumen in a minimally invasive surgical procedure.

The valve frame desirably is also configured to be longitudinally collapsible by folding the commissure posts inwardly toward a sewing ring of the valve. During implantation of the valve, the commissure posts can be retained in the longitudinally collapsed state to provide the surgeon greater access to the sewing ring for suturing (or otherwise securing) the sewing ring to the native annulus. After the valve is secured to the native annulus, the commissure posts can be released from the collapsed state so as to allow the commissure posts to self-expand to a deployed, functional state.

The commissure posts, in the deployed state, extend longitudinally from the sewing ring and can extend radially outward relative to a longitudinal axis of the valve. The outward lean of the commissure posts allow the leaflets to open to a relatively larger outlet opening during systole, thereby reducing the pressure gradient across the valve compared to commissure posts that are parallel to the longitudinal axis of the valve. In addition, the commissure posts can flex slightly inwardly and outwardly relative to the longitudinal axis of the valve during the cardiac cycle, which allows the leaflets supported by the commissure posts to close more gently and relieves stress on the leaflets during diastole.

In one representative embodiment, a prosthetic valve comprises an inflow end and an opposing outflow end defining a valve axis extending longitudinally of the ends, and a plurality of valve leaflets. The valve also comprises a collapsible, self-expandable frame assembly configured to support the valve leaflets and defining a plurality of commissure portions, and a sewing ring portion configured to secure the valve to a surrounding lumen, wherein the plurality of commissure portions are configured to move independently of the sewing ring when the valve is so secured.

In another representative embodiment, a prosthetic-valve delivery system comprises a prosthetic valve and a delivery device. The prosthetic valve is collapsible and expandable between a collapsed delivery configuration and a neutral configuration. The valve also comprises a sewing ring configured to be secured to an implantation site, and a resilient frame configured to cause the valve to expand from the collapsed delivery configuration to the neutral configuration. The delivery device is configured to assist the delivery of the valve to the implantation site when the valve is in the collapsed delivery configuration.

In another representative embodiment, a method of implanting a prosthetic valve at an implantation site within a body lumen is provided. The valve comprises a resilient frame and a sewing ring, and is configured to at least partially self-expand to a neutral configuration from a collapsed delivery configuration. The method comprises retaining a valve in a collapsed delivery position, making an incision in a body lumen adjacent an implantation site, inserting the collapsed valve through the incision, securing the sewing ring to surrounding tissue within the body lumen, and releasing the valve from the collapsed delivery configuration such that the valve independently recovers to the neutral configuration within the body lumen.

The foregoing and other objects, features, and advantages of the invention will become more apparent from the following detailed description, which proceeds with reference to the accompanying drawings.

BRIEF DESCRIPTION OF THE DRAWINGS

FIG. 6A shows systole and FIG. 6B shows diastole.

FIG. 8 illustrates a collapsible, self-expandable wireform frame of the type incorporated in the valve shown in FIG. 5. FIG. 8A is a side view of a commissure portion of the wireform frame illustrated in FIG. 8.

FIG. 9 shows the wireform frame shown in FIG. 8 in an axially (or longitudinally) collapsed position.

FIG. 10 shows FIG. 8 superimposed on FIG. 9, illustrating the extent to which the disclosed frame can elastically collapse in an axial (or longitudinal) direction relative to the uncollapsed position.

FIG. 11 shows the wireform frame in FIG. 8 in a radially collapsed position.

FIG. 12 shows a top plan view of the frame shown in FIG. 8.

FIGS. 14-27 show several intermediate constructs arising from several techniques for manufacturing a frame of the type shown in FIG. 8.

FIG. 14 shows a sheet of material from which a disclosed frame can be formed, such as by laser-cutting.

FIG. 15 shows a laser-cut flat pattern formed from the sheet shown in FIG. 14.

FIG. 16 shows a hollow cylinder (a tube) from which a disclosed frame can be laser-cut.

FIG. 17 shows a laser-cut cylindrical pattern formed from the hollow cylinder shown in FIG. 16.

FIG. 18 shows a laser-cut pattern (e.g., as shown in FIG. 15 or FIG. 17) in a first shape-setting position on a first mandrel.

FIG. 19 shows the laser-cut pattern shown in FIG. 18 in a second shape-setting position on a second mandrel.

FIG. 20 shows an isometric view of a finished frame of the type shown in FIG. 8.

FIG. 21 shows a wire from which a disclosed frame can be formed.

FIG. 22 shows the wire shown in FIG. 21 on a first wireforming mandrel.

FIG. 23 shows the wire after forming and shape setting and removal from the mandrel shown in FIG. 22.

FIG. 24 shows the formed wire shown in FIG. 23 on a second wireforming mandrel, similar to the mandrels shown in FIGS. 18 and 19.

FIG. 25 shows the wire after undergoing a shape setting process and removal from the mandrel shown in FIG. 24.

FIG. 26 shows a crimp sleeve for joining opposing ends of the formed wire.

FIG. 27 shows a completed wireform frame of the type shown in FIG. 8.

FIG. 28 shows a plan view of a leaflet as disclosed herein positioned beneath a conventional leaflet. As shown in FIG. 28 and discussed more fully below, the disclosed leaflet has a varying radius of curvature and a corresponding broader body relative to the conventional leaflet.

FIG. 29 shows a leaflet as disclosed herein.

FIG. 30 shows an isometric view of the frame shown in FIG. 8 partially covered by a cloth frame cover.

FIG. 31 shows an isometric view of the frame shown in FIGS. 8 and 23 covered by the cloth frame cover shown in FIG. 30.

FIG. 32 shows an exploded view of an assembly comprising the covered frame shown in FIG. 31 and three leaflets of the type shown in FIG. 29.

FIG. 33 shows an isometric view of the assembly shown in FIG. 32.

FIG. 34 shows a top plan view from above the assembly shown in FIGS. 25 and 26.

FIG. 35 shows a top plan view from below the assembly shown in FIGS. 25 and 26.

FIG. 36 shows an isometric view of a collapsible stent as disclosed herein.

FIG. 37 shows an isometric view of the collapsible stent shown in FIG. 36 in an axially (or longitudinally) collapsed position.

FIG. 38 shows a side elevation view of the axially collapsed stent shown in FIG. 37.

FIG. 39 shows an isometric view of a sewing ring insert as disclosed herein.

FIG. 40 shows a side elevation view of the sewing ring insert shown in FIG. 39.

FIG. 41 shows an exploded view of a partial assembly comprising the stent shown in FIG. 36, the sewing ring insert shown in FIG. 39 and a tubular covering cloth for joining the stent and the sewing ring insert as shown, for example, in FIG. 7.

FIGS. 42A-42C show various views of a prosthetic valve mounted on a valve holder that can be used to deliver a valve to an implantation site. The illustrated holder retains the commissure portions of the valve in at least a partially collapsed configuration, which allows for increased access to the sewing ring portion of the valve for attachment to the native annulus during implantation. FIG. 42C shows the valve in a partially "ovaled" configuration for easier insertion through a narrow surgical opening, such as a thoracotomy.

FIG. 42D shows a delivery device comprising the valve holder, shaft and handle attached to the shaft opposite the valve holder.

DETAILED DESCRIPTION

Figure 1:
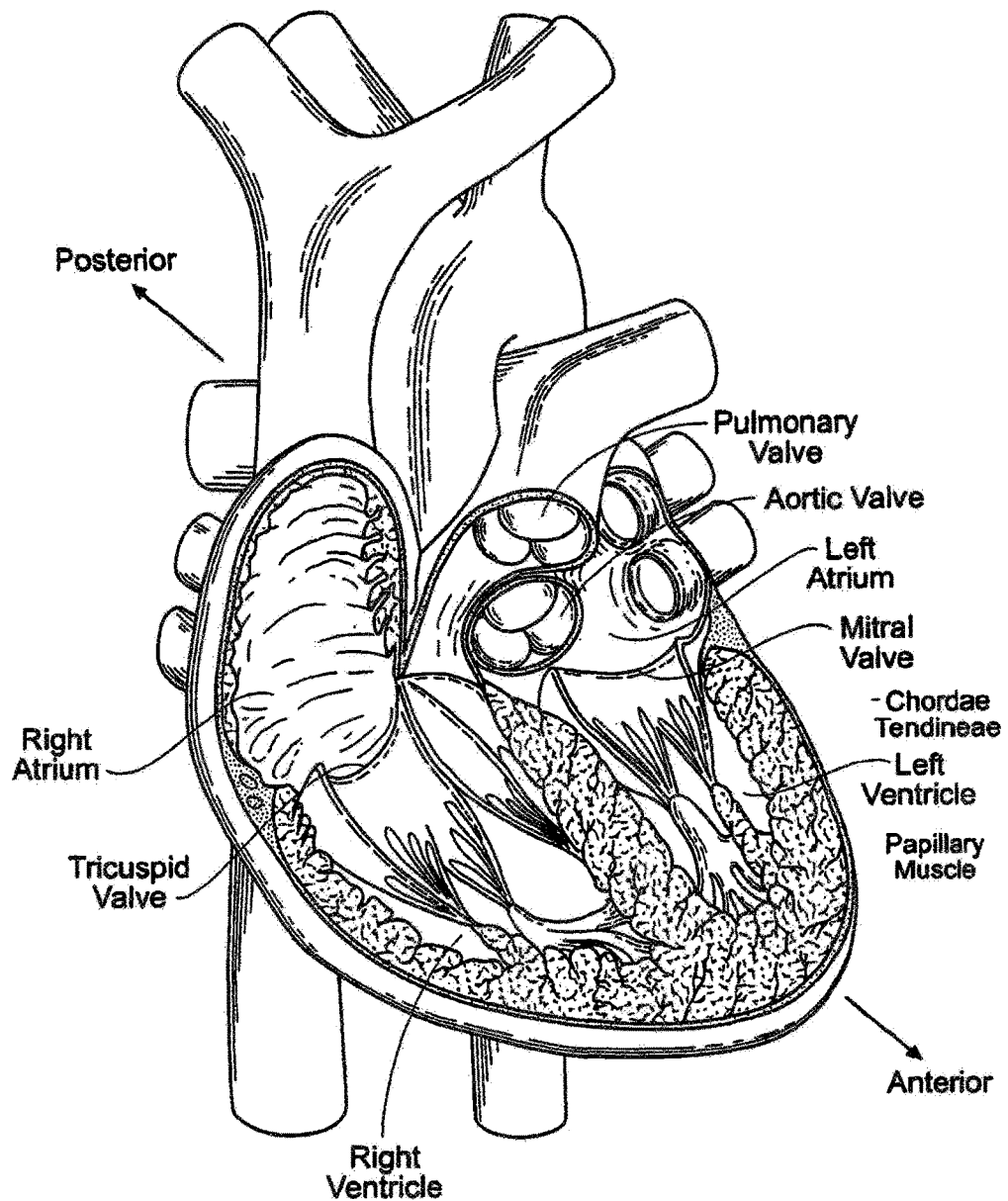
FIG. 1 illustrates an anatomic anterior view of a human heart, with portions broken away and in section to view the interior heart chambers and adjacent structures.
Figure 2:
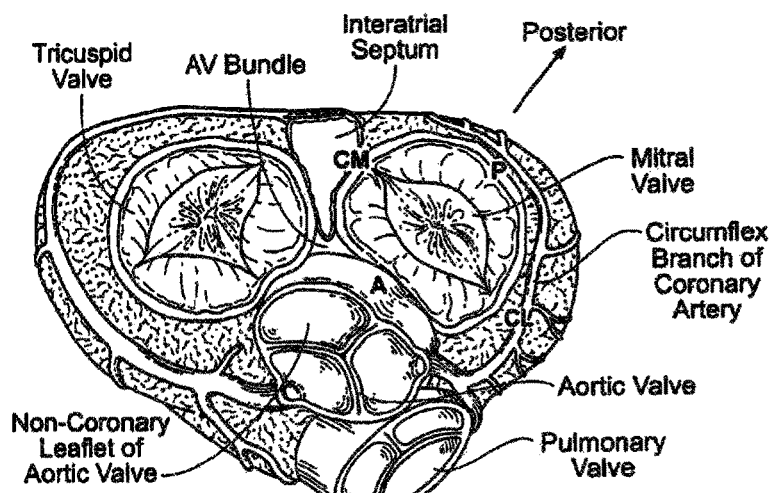
FIG. 2 illustrates an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
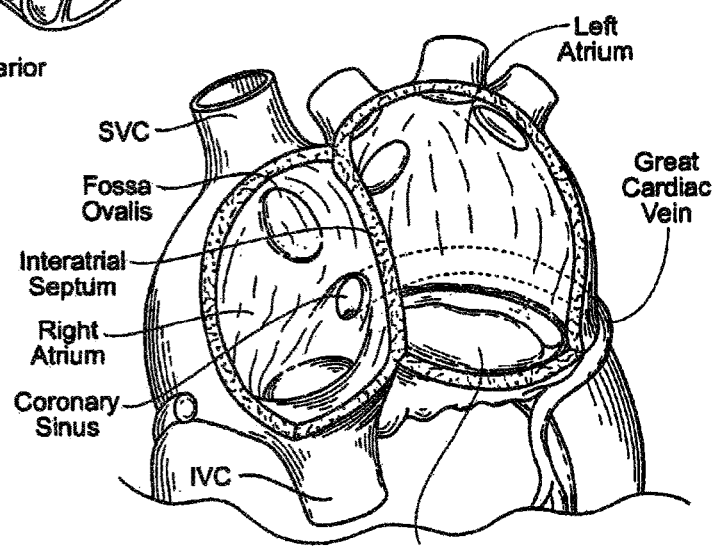
FIG. 4 shows an anatomic anterior perspective view of the left and right atria, with portions broken away and in section to show the interior of the heart chambers and associated structures, such as the fossa ovalis, coronary sinus and the great cardiac vein.
Figure 3:
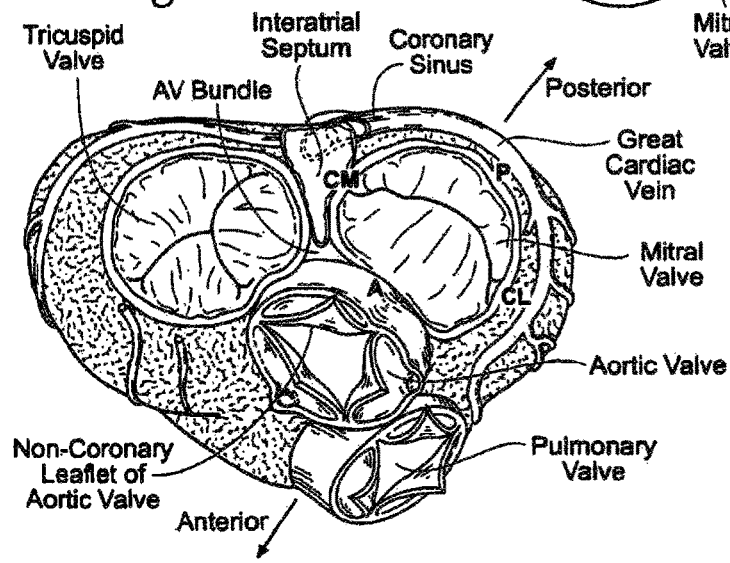
FIG. 3 shows an anatomic superior view of a section of the human heart shown in FIG. 2, with the tricuspid and mitral valves closed and the aortic and pulmonary valves open during ventricular systole (ventricular emptying) of the cardiac cycle.

The following describes principles related to implantable prosthetic valves and related methods and systems with reference to exemplary prosthetic valves, delivery systems, and manufacturing and assembly methods. One or more of the disclosed principles can be embodied in many different configurations to accommodate various design objectives. Some disclosed valves and delivery systems can be used in conjunction with minimally invasive surgical techniques. However, prosthetic cardiac valves and delivery systems compatible with minimally-invasive surgical (MIS) techniques are but examples of the wide variety of prosthetic valves and related methods and systems incorporating the principles disclosed herein.

Overview

As described more fully below and shown in the accompanying drawings (e.g., FIGS. 5A and 5B), valves as disclosed herein can comprise a resiliently collapsible frame in combination with a valve securing portion (e.g., an annular sewing ring) for securing the valve to the tissue of a surrounding body lumen. Such frames allow disclosed valves to be retained in a collapsed deployment configuration so as to provide, among many advantages, convenient access to the securing portion, while maintaining the ability to self-expand upon being released from the deployment configuration.

As used herein, "self expand" means to elastically recover from a collapsed (e.g., a compressed) configuration when an external restraint (e.g., a suture, a sheath or a holder) is removed.

As used herein, a "neutral position" or a "neutral configuration" means a configuration of a valve and/or a frame when the respective valve and/or frame is at-rest (e.g., still) and free from externally applied loads (e.g., pressure gradients through the valve, forces applied by retaining and/or delivery devices to retain the valve in a collapsed configuration).

As used herein, a "deployed neutral configuration" means a configuration of a valve and/or a frame when the respective valve and/or frame is in an expanded state within a body lumen during implantation and is free from externally applied loads (e.g., pressure gradients through the valve) other than those external forces resulting, at least in part, from contact with a surrounding tissue.

As used herein, an "implanted neutral position" or an "implanted neutral configuration" means a configuration of a valve and/or a frame when the valve is implanted in a body lumen and secured to surrounding tissue, and is free from externally applied loads (e.g., pressure gradients through the valve) other than those external forces resulting, at least in part, from attachment to the tissue. Stated differently, an "implanted neutral configuration" means the expanded configuration of the valve immediately following implantation.

In many instances, a valve's neutral configuration and implanted neutral configuration are substantially the same configuration, but this need not be the case (e.g., a valve can be slightly over-sized relative to the surrounding tissue of a body lumen, such that forces applied by the surrounding tissue slightly deforms the valve in its implanted neutral configuration, relative to the neutral position). As discussed below and shown in FIGS. 6A and 6B, the valve configuration changes from the implanted neutral configuration during diastole and systole.

Some resilient support structures (or frames) allow the support structure to resiliently expand between a substantially collapsed configuration (e.g., a delivery configuration as shown in FIGS. 9 and 11) and a substantially undeformed, neutral position (e.g., FIG. 8). Some frames comprise a super-elastic material (e.g., a shape-memory material). Nitinol is an alloy comprising nickel and titanium (e.g., between about 55% and about 57% nickel combined with a minimum of about 42.85% titanium by weight, and traces (i.e., up to about 0.05% by weight) of carbon, oxygen and iron) that demonstrates super-elasticity (i.e., can elastically deform through strains as large as between about 8% and about 10%).

Figure 5A:
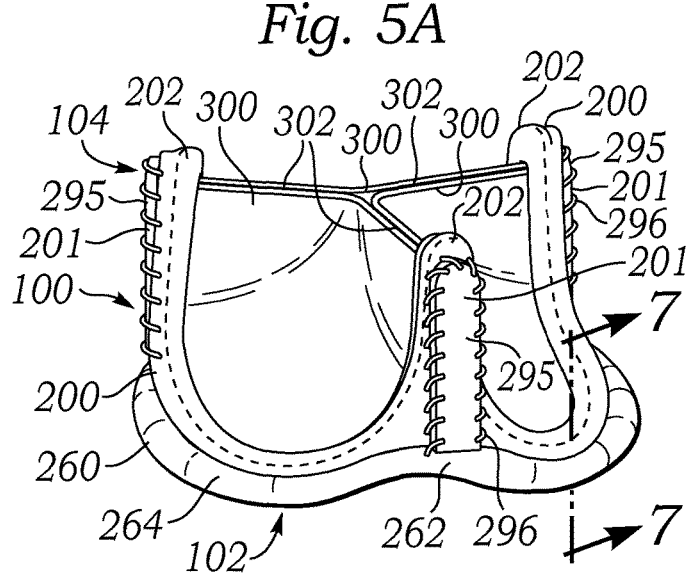
FIG. 5A illustrates an isometric view of one embodiment of a prosthetic valve of the type disclosed herein (e.g., a prosthetic aortic valve).
Figure 5B:
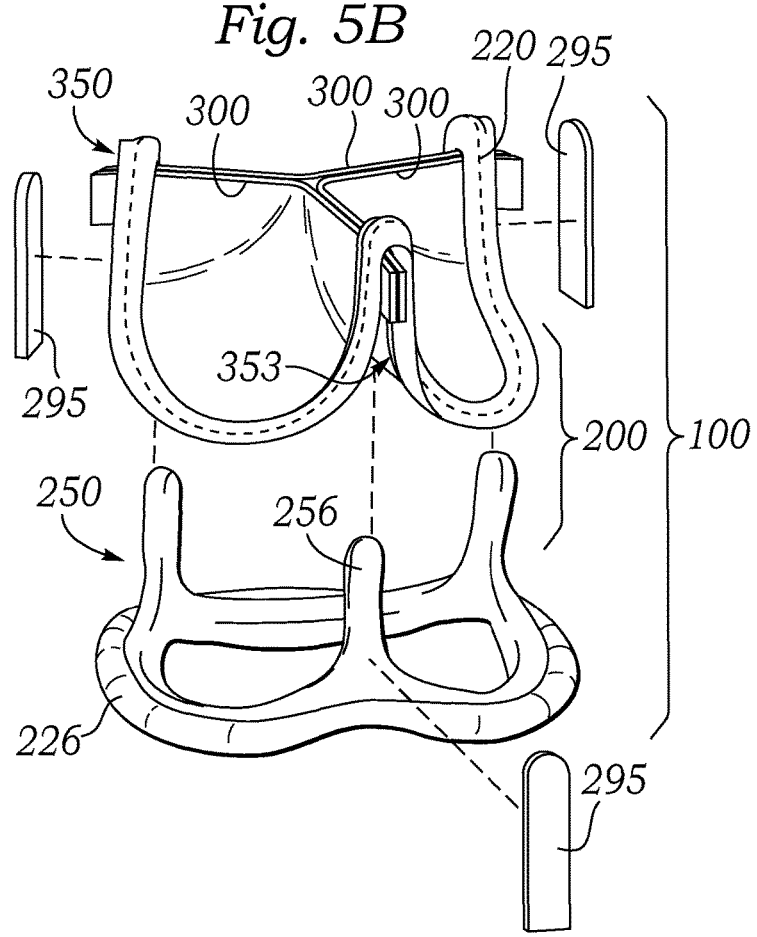
FIG. 5B shows a partially exploded view of the prosthetic valve assembly shown in FIG. 5A.
Figure 6A:
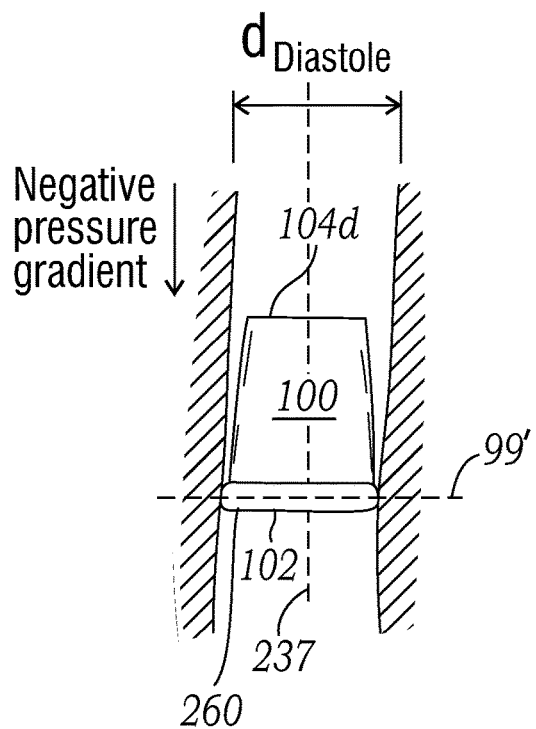
FIGS. 6A and 6B are schematic longitudinal cross-sectional views of the valve shown in FIGS. 5A and 5B installed in, for example, an aortic annulus.
Figure 6B:
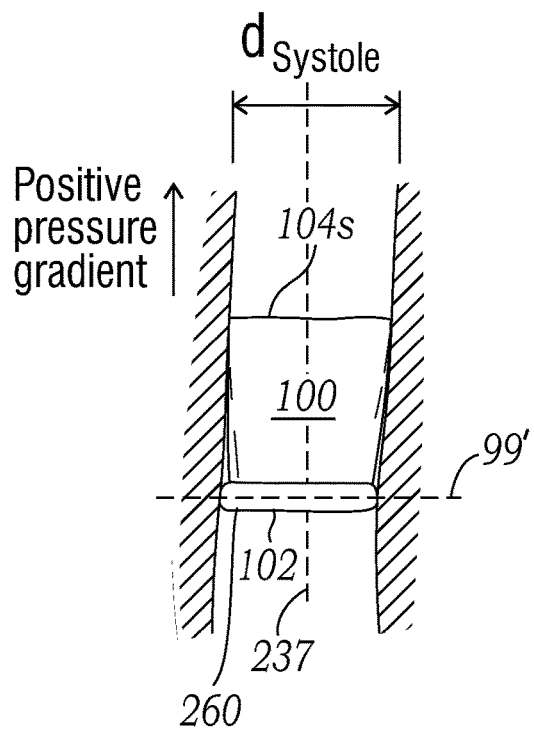
Figure 7:
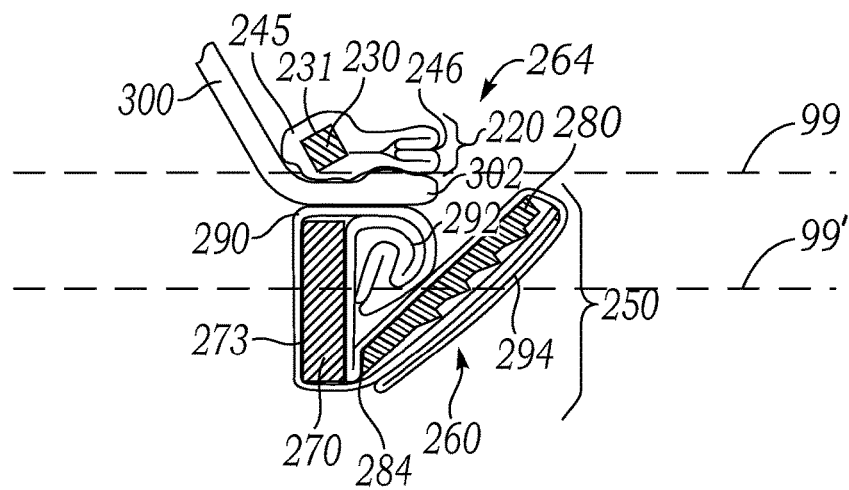
FIG. 7 shows a cross-sectional view taken along section line 7-7 shown in FIG. 5.

The valve 100 shown in FIGS. 5A and 5B has an inlet end 102 and an outlet end 104, a cloth-covered frame assembly 200 defining commissure posts 201 (also referred to herein as commissure portions) of the valve and three leaflets 300 coupled to the frame assembly. In the illustrated embodiment, the commissure posts 201 of the valve lean slightly outward relative to a central flow axis of the axis of the valve when the valve is in its neutral configuration. During diastole, the outlet end 104 can contract such that the commissure posts lean inward of a neutral position to define a diameter, $D_{diastole}$ at the outlet end of the valve that is slightly less than the diameter, $D_{systole}$, at the outlet end during systole, as shown in FIGS. 6A and 6B. As shown in FIGS. 7 and 33, the illustrated frame assembly 200 comprises a cloth-covered stent and sewing ring sub-assembly 250 having a suture-permeable, annular sewing ring 260 extending circumferentially around the inlet end 102 of the valve 100. A valve attachment portion, such as the illustrated annular sewing ring 260, can lie in a substantially common plane 99' with the inlet end 102 when the valve is in a neutral position, as shown in FIG. 7.

As discussed more fully below, the frame assembly 200 can be pliant and can undergo substantial deformation from the neutral position shown in FIG. 5, allowing the frame 200 to be resiliently collapsed to a smaller size for delivery (e.g., the commissure tips 202 can move radially inward into a delivery position), and to self-expand from such a collapsed position (e.g., the commissure tips 202 can move radially outward at least in part due to the resiliency of the frame). Since the valve 100 is secured to a lumen by the stent and sewing ring subassembly 250, the commissure tips 202 remain free to move relative to the sewing ring. The leaflets 300 can open when exposed to a positive pressure gradient in a fluid (e.g., blood) passing between the inlet end 102 and the outlet end 104 and close (or coapt) when exposed to a negative pressure gradient between the inlet end and the outlet end.

In other valves, the circumferentially extending sewing ring 260 (or other attachment portion) need not be located adjacent the inlet end 102 and can be longitudinally spaced therefrom (e.g., the attachment portion can be positioned between the inflow end and the outflow end). Disclosed attachment portions also need not lie entirely within a given plane 99'. In any event, and as more fully described below, disclosed valves comprise an attachment portion having a sufficiently low profile (relative to the overall length of the valve) to allow respective commissure portions of the valve (e.g., the commissure tips 202) to move independently of the attachment portion.

Once a disclosed valve 100 is positioned at an implantation site, the circumferentially extending attachment portion can engage and/or be attached to an inner periphery of the body lumen (e.g., a native annulus) at the implantation site. For example, disclosed prosthetic valves can be implanted in the aortic annulus, and the annular sewing ring can be attached (e.g., sutured) to the fibrous annulus, or to the aorta wall, at a position downstream from the location of the natural leaflets. Various forms of attaching the annular sewing ring to the fibrous annulus and/or aorta can be used, such as sutures, staples, adhesives and/or similar expedients.

Positioning the attachment portion relative to the valve body and the implantation site, as just described, can allow portions of the frame (e.g., the cantilevered commissure portions 201 that extend longitudinally of the sewing ring 260) to deflect independently of the surrounding body lumen to which the valve is secured. Such independent deflection provides several advantages. For example, cantilevered support structure of some disclosed valves can lean radially outward in an undeformed, neutral position, providing a larger outlet orifice for the valve and a lower pressure gradient within a fluid passing through the valve. Nonetheless, outwardly leaning support structure can obstruct access to a securing portion (e.g., sewing ring) when the valve is in a neutral position. In disclosed valves, such outwardly leaning (or neutral or inwardly leaning) cantilevered support structure can be retained radially inward of the valve securing portion during implantation, providing convenient access to the securing portion.

Body lumens, and in particular orifices of the heart, dilate and contract with the cardiac cycle, as will now be described with reference to FIGS. 6A and 6B. Some disclosed valves 100 can be so configured as to flexibly accommodate such radial contraction, as occurs during diastole and dilation, as occurs during systole.

In some disclosed valves, the sewing ring 260 remains substantially undeformed during the cardiac cycle. In particular embodiments, the commissure portions 201 of the valve are cantilevered and can flex with respect to the sewing ring 260 and the prosthetic valve 100 and its low-profile sewing ring 260 can be secured to the lumen within, or substantially adjacent to, a plane 99'. Typically, the pressure gradient across the valve during systole is small enough (e.g., less than 10 mmHg in some embodiments) that the commissure portions remain in the neutral configuration and define a diameter at outlet end of the valve (referred to as systolic diameter $D_{systole}$ in FIG. 6B). On the other hand, during diastole, the pressure gradient across the valve causes the commissure portions to flex inwardly slightly so as to define a diameter at the outlet end of the valve (referred to as diastolic diameter $D_{diastole}$ in FIG. 6A), smaller than the systolic diameter. Accordingly, the diameter measured between the commissure portions at the outlet end 104 of the frame assembly can remain free to dilate and contract during the cardiac cycle. The ability of the commissure portions to flex in this manner allows the leaflets supported by the commissure portions to close more gently and relieves stress on the leaflets during diastole. In some implementations, the commissure portions can be configured to flex outward from the neutral configuration during systole (i.e., the commissure portions can flex further outward at the outlet end of the valve compared to their configuration shown in FIG. 6B).

Moreover, because there is a lack of direct connection between the outlet end 104 and the adjacent lumen (e.g., the aortic wall), the lumen can dilate naturally and without being constrained by the prosthetic valve 100 or its frame 200. For example, when a lumen dilates, points on an inner circumference of the lumen translate circumferentially with regard to each other (e.g., such points move farther apart from each other as the lumen dilates). In contrast, valve outlets secured to an interior of the lumen can resist (or constrain) the natural dilation of the lumen over a significant portion of the length of the valve. By eliminating a direct connection between the outlet end 104 of the prosthetic valve 100 and the surrounding lumen, the lumen can remain substantially free to dilate naturally over a majority of the length of the valve. In some embodiments, the diastolic diameter of the valve (FIG. 6A) is smaller than the outer diameter at the outlet end of the valve in a neutral configuration due, at least in part, to the resiliency and the flexibility of the commissure portions of the valve frame. Such dilation can relieve stress on the leaflets during the cardiac cycle. In some embodiments, the systolic diameter is larger than the outer diameter at outlet end of the valve when the valve is in a neutral (e.g., an implanted neutral) configuration.

In operation, seams between adjacent leaflets 300 can separate under a positive pressure gradient through the valve (e.g., during systole) and coapt under a negative pressure gradient through the valve (e.g., during diastole). In some disclosed valves, such separation and coaptation can be improved by allowing radial movement of the commissure portions 201 (e.g., corresponding to dilation and contraction of the body lumen) relative to the sewing ring 260.

Frame

As used herein, "wireform frame" (also sometimes referred to herein as a "wireform" or "wireform stent" means a three-dimensional body formed of one or more wires or similarly shaped elongate members. In some frames, each of the one or more members has a substantially constant cross-sectional shape along its length. By way of example, such an elongate member can have a substantially solid, rectangular (e.g., square) cross-sectional shape (e.g., as shown in FIG. 7). Other cross-sectional shapes (e.g., circular, annular, hollow rectangle) are also possible. U.S. Pat. No. 6,558,418 describes a frame comprising more than one elongate member that can be implemented in the valve 100, and is incorporated herein in its entirety. Also, the stent, or frame, of the valve need not be a "wireform" frame formed from wires. For example, the frame of the valve can be cut or otherwise formed from tubing or a sheet of material and the individual components of the stent can have various cross-sectional shapes.

FIG. 7 shows a partial cross-sectional view through a cusp region 264 of the valve 100. As shown in FIG. 7, the frame assembly 200 can comprise a cloth-covered wireform sub-assembly 220 (FIG. 5B) and a cloth-covered stent and sewing ring sub-assembly 250 (FIG. 5B). The frame assembly 200 can retain respective peripheral portions 302 of three leaflets 300 between the cloth-covered wireform subassembly 220 and a cloth-covered stent portion 270 (FIG. 33) of the stent and sewing ring sub-assembly 250.

The illustrated cloth-covered wireform portion 220 comprises a wireform frame 230 (FIG. 8) and a wireform cover 245 (FIG. 30). As shown in FIG. 7, the cover 245 surrounds the outer surface 231 of the wireform 230 and forms a seam 246 externally of the wireform in a region adjacent the peripheral portion 302 of the leaflet 300 on a side of the leaflet positioned opposite the stent and sewing ring sub-assembly 250.

The illustrated stent and sewing ring subassembly 250 comprises a stent 270 (FIG. 36) and a sewing ring insert 280 (FIG. 39) joined and covered by a rolled stent covering cloth 290 (FIG. 41). In an alternative embodiment, the stent and sewing ring subassembly 250 can comprise a stent 2600 (FIG. 45) and the sewing ring insert 280 (FIG. 39) joined and covered by a rolled stent covering cloth 290 (see FIG. 41 and FIG. 46). The sewing ring portion 260 (e.g., the sewing ring insert 280 and the adjacent cloth 290) can be suture permeable (e.g., sutures can extend through the sewing ring) and can provide an attachment region for attaching the valve 100 to a surrounding region of a body lumen (not shown).

One embodiment of a wireform frame 230 is shown in FIG. 8. The illustrated wireform 230 comprises a continuous elongate member and a plurality of cusp portions 232 spaced from each other by respective, longitudinally extending commissure portions 233. Each commissure portion 233 comprises a pair of opposing commissure posts 234 extending from their proximal ends adjacent respective cusps 232 to distal ends joined to each other by a corresponding commissure tip 235. The illustrated commissure tips comprise a single, narrow arcuate segment defining an upwardly convex arcuate tip. (Other commissure tips can comprise a pair of upwardly convex arcuate portions separated by an upwardly concave intermediate region, giving such a commissure tip the appearance of "mouse ears," as disclosed in U.S. Pat. No. 7,473,275, which is incorporated herein in its entirety.) The proximal end of each commissure post 234 is joined to a respective cusp portion 232.

The wireform frame 230 shown in FIG. 8 has three cusp portions 232 separated by three respective commissure portions 233. Other numbers of commissure portions (e.g, 2, 4, 5, etc.) are also possible. The elongate member forming the wireform frame 230 shown in FIG. 8 has a substantially square cross-sectional shape (FIG. 7).

As shown in FIGS. 5A, 5B, 8 and 12, each cantilevered commissure portion 233 extends substantially vertically from (e.g., longitudinally of) the cusp portions 232 so as to define an inner, substantially cylindrical region 236 of the frame. In other words, the tips 202 of the commissure portions are distally located relative to the cusp portions and an attachment portion (such as, for example, the sewing ring 260). That is to say, the commissure portions 233 are cantilevered such that the tips 202 are free ends of the cantilevered structure. Such cantilevered commissure portions 233 can allow the attachment portions of disclosed valves to be secured at an implantation site while the valve is in a collapsed delivery position, as further described below. The inner, substantially cylindrical region 236 of the frame defines a longitudinal axis 237 of the frame extending therethrough.

Each cusp portion 232 comprises a broad arcuate segment extending between proximal ends of the commissure posts 234 adjacent the respective cusp portion. A plane 99 oriented substantially perpendicular to the longitudinal axis 237 of the frame 230 can be substantially tangent to each of the cusp portions 232, as shown in FIG. 8. In some embodiments, a transverse cross section of the sewing ring 260 (FIG. 6) (a cross section substantially perpendicular to the longitudinal axis 237) can lie entirely within a plane 99' substantially parallel to the plane 99. In any event, the sewing ring 260 and the corresponding region of attachment to the body lumen have sufficiently low-profiles as to allow the cantilevered commissure portions 233 to flex, as discussed above.

Although the commissure portions 233 extend substantially vertically (axially) from the cusp portions 232 (e.g., are cantilevered), the commissure portions can be oriented to lean inwardly or outwardly at a slight angle α relative to the longitudinal axis 237 (sometimes referred to as a "valve axis"). For example, when in a neutral configuration 238 as shown in FIGS. 8 and 8A, the commissure portions 233 can extend radially outward of the cusp portions 232 (i.e., radially away from the longitudinal axis 237) at an angle in the range of about 1 degree to about 5 degrees, with 2 degrees being a specific example. In other embodiments, the commissure portions 233 extend radially inward of the cusp portions 232 toward the longitudinal axis 237 of the frame, for example, at an angle in the range of about 1 degree to about 5 degrees when in the neutral position 238.

Such inwardly and/or outwardly leaning, neutrally positioned commissure portions 233, when incorporated into an assembled prosthetic valve (e.g., the valve 100), can provide improved hemodynamics through the valve. In other words, the extent to which the commissure portions 233 lean inwardly or outwardly in the neutral position (and/or implanted neutral configuration) can be adjusted, together with the leaflet design (described below), to obtain desired pressure gradients through the valve throughout the cardiac cycle when the valve is implanted.

As noted above, wireform frames can be formed from a super-elastic material, such as, for example, Nitinol. Techniques for forming such wireform frames are described more fully below with regard to FIGS. 14-20. When formed of a super-elastic material, the wireform 230 can be elastically collapsed (e.g., longitudinally and/or radially) to a significant degree (FIG. 9) without damaging the wireform (e.g., without plastically deforming or fracturing the wireform). Such a collapsed frame can self-expand and recover its original neutral configuration (e.g., FIG. 8). Other frame forming techniques are disclosed in U.S. Patent Publication 2004/0078950, which is hereby incorporated by reference in its entirety.

In FIG. 9, the wireform frame 230 shown in FIG. 8 is shown in a fully longitudinally collapsed position 239 (e.g., for delivery) from which the frame can self-expand to the neutral configuration 238 shown in FIG. 8. In the longitudinally collapsed position 239, the frame's commissure tips 235 (corresponding to the valve's commissure tips 202 shown in FIGS. 5A and 5B) are folded radially inward toward the longitudinal axis 237 (FIG. 8) and relative to the cusp portions 232 until the tips 235 reach respective collapsed positions 235' (FIG. 9). Respective upward facing regions of the cusp portions 232 "roll" slightly inward toward the longitudinal axis 237 to a longitudinally-collapsed cusp position 232' when the commissure tips are in their respective longitudinally collapsed positions 235'. In this collapsed position 239, the interior 236 of the frame 230 becomes a substantially conical shape 236' as compared to the substantially cylindrical shape defined by the frame in the neutral position 238.

FIG. 10 shows a comparison of the neutral position 238 and the fully longitudinally collapsed position 239 of the wireform frame 230 shown in FIG. 9. As discussed more fully below, a prosthetic valve 100 (FIGS. 5A and 5B) in a longitudinally collapsed position 239, as shown in FIG. 9, allows convenient access to an inlet end 102 of the valve and/or a sewing ring portion 260 for securing the valve 100 to a body lumen without interference by the commissure portions 233. In other words, by folding the commissure portions inwardly as shown in FIG. 9, the commissure portions (which may be outwardly leaning when the valve is in a neutral configuration, as shown in FIG. 8) do not interfere with access to the sewing ring portion 260, allowing the valve to be more quickly secured (e.g., sutured) to a surrounding tissue.

FIG. 11 shows a plan view from above the wireform frame 230 in a fully radially-collapsed position 240 (e.g., for delivery) from which the frame can self-expand to the undeformed, neutral configuration 238 shown in FIG. 8 and FIG. 12. In the context of the wireform 230, radially collapsed means that base of at least one of the commissure portions 233 of the wireform 230 is displaced radially inwardly from the neutral configuration 238 shown in FIG. 12 toward the longitudinal axis 237 and/or toward an opposing cusp 241 to a radially collapsed position 233" (so as to decrease a diameter and/or a spacing between the commissure portion 233 and a diametrically opposing location on the frame 230), while the remaining commissure portions are left substantially free to twist into a buckled configuration 242. Stated differently, the frame 230 can be placed to the radially collapsed configuration by pinching the frame at two diametrically opposed locations adjacent the inflow end of the frame. In the radially collapsed configuration 240, the interior volume 236" of the frame can become a substantially oval prism as shown, rather than a cylinder (or circular prism), as in the neutral configuration.

Figure 13:
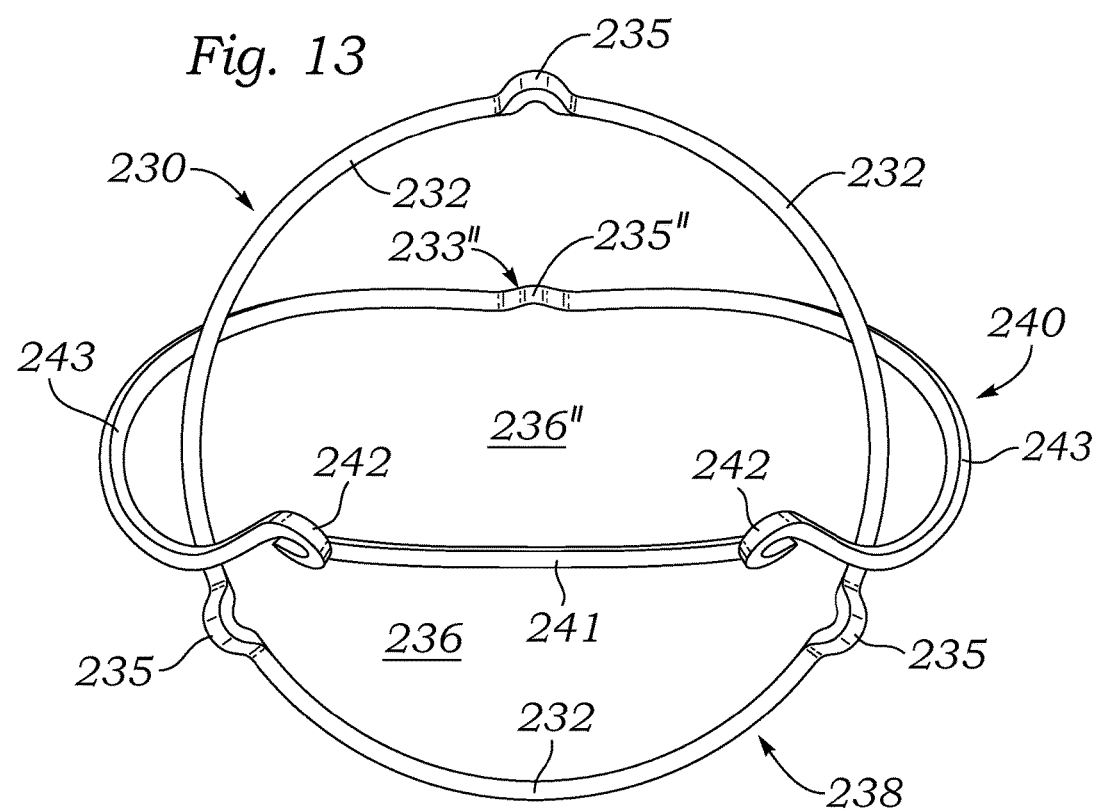
FIG. 13 shows FIG. 11 superimposed on FIG. 12, illustrating the extent to which the disclosed frame can elastically collapse in a radial direction relative to the uncollapsed position.

FIG. 13 shows FIG. 11 and FIG. 12 superimposed on each other and illustrates the relative extent to which the radially collapsed position 240 differs from the neutral position 238. As best seen in FIG. 13, cusps 243 positioned on opposing sides of the commissure portion 233 can bulge outwardly as compared to the same cusps 243 when the valve is in the neutral position. Similarly, the cusp 241 can deflect inwardly to a flattened position. Such a radially collapsed position 238 can allow a valve 100 (FIGS. 5A and 5B) to more easily pass through an incision in a minimally invasive surgical technique, such as a thoracotomy and/or an aortotomy (e.g., by "shoe-horning" the valve through the incision, as described more fully below).

With reference to FIGS. 14-27, several possible techniques for forming a wireform frame 230 will now be described. As shown in FIG. 14, the frame 230 can be formed starting with a sheet material 410. A laser cutting process 415 can be applied to the sheet material 410 to form a laser cut flat pattern 420, as shown in FIG. 15. In alternative embodiments, the pattern for forming the frame can be formed from a sheet material 410 or tubing, using other suitable techniques, such as stamping, water-jet cutting, or chemical etching.

The exemplary flat pattern 420 shown in FIG. 15 comprises broad outwardly convex portions 422 that comprise the cusps 232 of the frame 230 shown in FIG. 8. Extending from opposing ends of the convex portions 422 are lengths 424 of the pattern that comprise the commissure posts 234 of the frame 230. As in the finished frame 230, distal ends of opposing lengths 424 are joined by respective outwardly concave, arcuate segments 426 that comprise the commissure tips 235 of the finished frame 230.

As an alternative to forming a wireform frame 230 starting with a sheet material, as just discussed, the frame can be formed starting with a hollow, cylindrical tube 430, as shown in FIG. 16. A laser-cutting process 435 can be applied to the tube 430 to form a laser-cut cylindrical pattern 440 as shown in FIG. 17. The cylindrical pattern 440 resembles the finished wireform frame 230 shown in FIG. 8. The cylindrical pattern comprises cusps 442 extending between commissure portions 443. The commissure portions 443 comprise opposing commissure posts 444 extending from respective cusps 442 at their proximal end to a distal end joined to an adjacent distal end by an arcuate commissure tip 445. At this stage, the cylindrical pattern 440 lacks any inward or outward taper a (FIG. 8) of the commissure portions 443, and has not yet undergone a shape setting process to provide the Nitinol pattern 440 with the shape memory of the finished wireform 230.

FIG. 18 shows a laser-cut pattern 420, 440 undergoing a first shape setting process while being supported by a first mandrel 450. The laser-cut pattern 420, 440 can be installed on a body 452 of the first mandrel such that cusp posts 453 engage respective cusp portions 422, 442 of the pattern 420, 440. The mandrel body 452 can have a cylindrical or frusto-conical outer surface. For example, the body 452 of the first mandrel can taper inwardly from a base adjacent the cusp posts 453 by about 5°. A first annular mandrel cover 454 having an interior surface contour (e.g., tapering by about 5°) (not shown) corresponding to the external contour of the mandrel body 452 can urge against the commissure posts 424, 444 of the pattern. In other words, the annular mandrel cover 454 defines an annular opening (not shown) between the cover and the mandrel body 452. The cut pattern 420, 440 is positioned within this annular opening.

Once positioned as just described, the pattern 420, 440, the mandrel and the mandrel cover can be heated treated to shape set the pattern 420, 440 to the desired shape. For example, the pattern 420, 440 can be heated to about 520 degrees Celsius (° C.) for about 8 minutes.

Afterward, the pattern 420, 440 can be placed on a second mandrel 460 (e.g., having body 462 with an outward taper (relative to the first mandrel body 452). In some instances, the outward taper of the second mandrel 460 is about 2° relative to a longitudinal axis of the mandrel (not shown). A second mandrel cover 464 having an interior contour (not shown) corresponding to the external contour of the second mandrel body 462 can be placed over the pattern 420, 440. The pattern can be heated, as described above. The two-step shape setting process described above is one example of a process that can be used to form the wireform 230. In other embodiments, shape setting can be accomplished in one step or more than two steps.

Following heating on the second mandrel 460, the pattern can be removed and undergo a finishing process 470 (e.g., microblasting and/or electropolishing). The completed wireform 480 shown in FIG. 20 has the features described in connection with the wireform 230 shown in FIG. 8.

Figure 21:
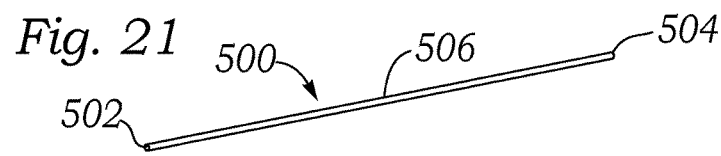

With reference to FIGS. 21-27, an alternative technique for forming the wireform 230 from a wire 500, such as, for example, a nitinol wire, will now be described. Referring to FIG. 21, the wire 500 has opposing first and second ends 502, 504 and a body 506 extending between the ends.

Figure 22:
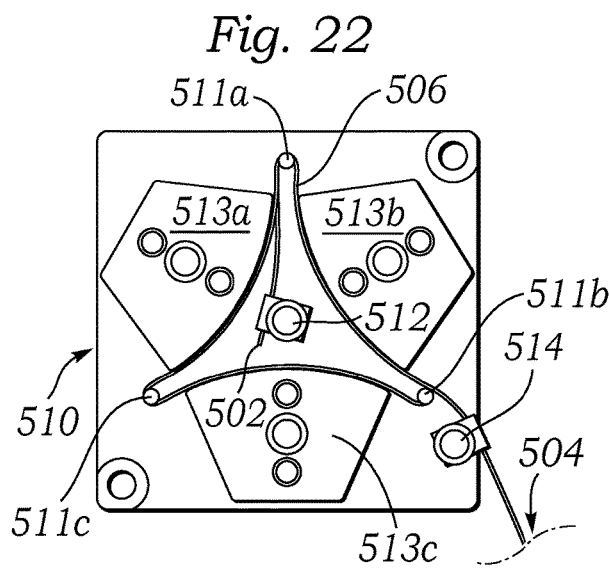

As shown in FIG. 22, the wire 500 can be installed on a first wireforming mandrel 510 by wrapping the body 506 around pegs 511a, 511b, 511c and securing the first end 502 in a clamp, or jaws, 512. Shaping features 513a, 513b, 513c can urge portions of the body 506 extending between the pegs 511a, 511b, 511c inwardly, as shown, to form concavely curved portions of the wire 500. The free second end 504 can be pulled taught such that slack in the wire body 506 is sufficiently removed. A second clamp, or jaws, 514 can tighten against the body 506 in a region adjacent the free second end 504.

Figure 23:
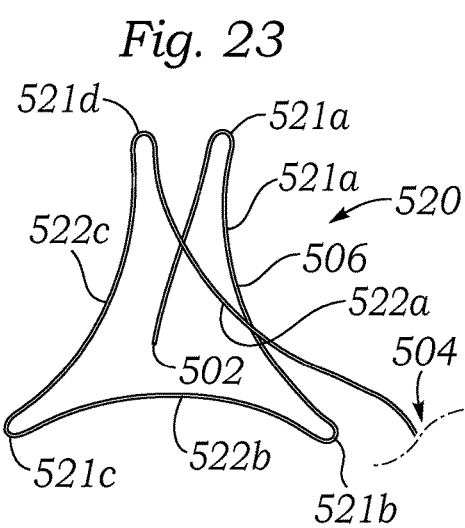

Once the wire 500 has been positioned on the first wireforming mandrel 510 as just described, the wire and the mandrel can be sufficiently heat treated such that the wire 500 substantially retains its on-mandrel form when removed from the mandrel 510, as shown in FIG. 23. For example, when removed from the mandrel 510, the wire 500 can define arcuate commissure tips 521a, 521b, 521c, 521d formed by the respective pegs 511a, 511b, 511c, 511a, and corresponding concave regions that form cusp portions 522a, 522b, 522c of the finished frame 560 (FIG. 27), as well as the concave portion 522d.

Figure 24:
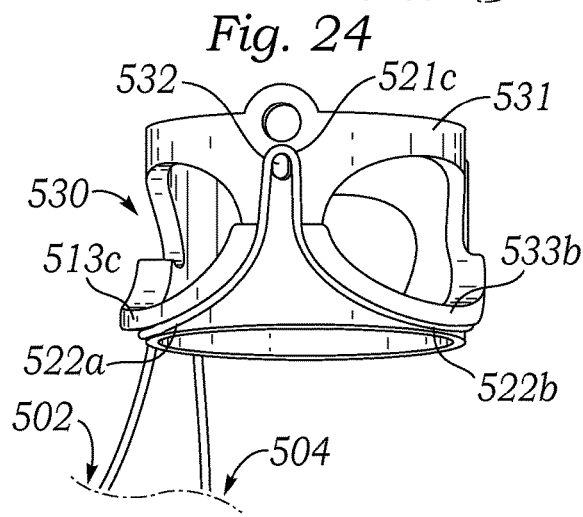

The shaped wire 520 is shown overlying a second wireforming mandrel 530 in FIG. 24. The mandrel's body 531 defines pegs 532 and guides 533b, 533c configured to hold the shaped wire 520 in position. For example, each of the commissure tips 521a, 521b, 521c, 521d can be positioned with each tip extending around a corresponding peg 532, with the tips 521a and 521d being positioned adjacent a single peg (not shown). In such a position, the opposing ends 502, 504 can extend downwardly of the second mandrel 530, as shown. The cusp portions 522a, 522b, 522c and concave portion 522d can also be positioned adjacent corresponding mandrel guides (of which only the guides 533b, 533c are shown).

Figure 25:
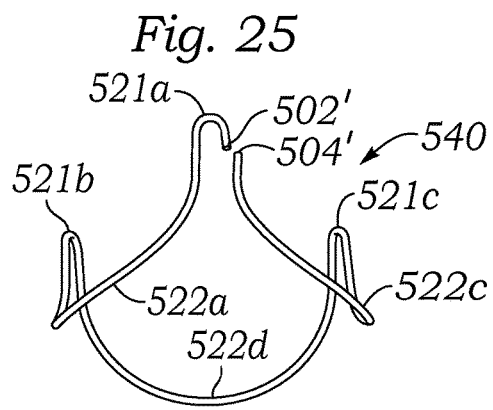
Figure 26:
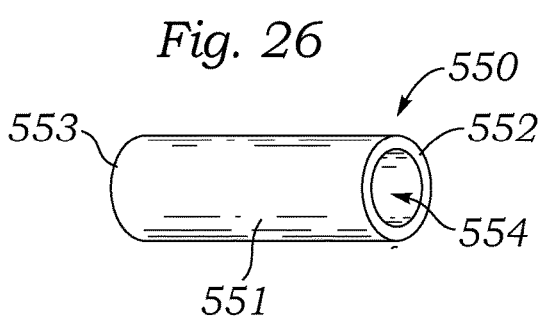
Figure 27:
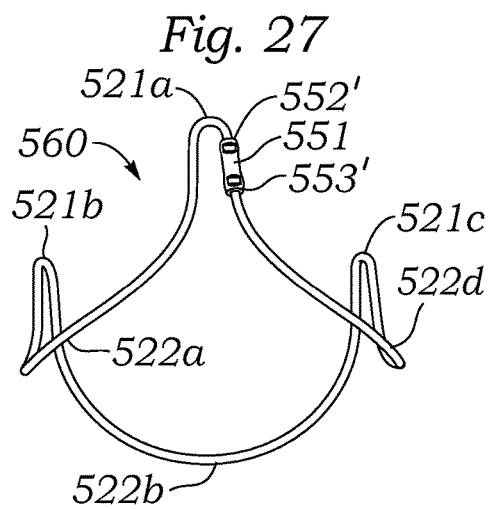

The shaped wire 520 and mandrel 530 can undergo a second heat treating process (e.g., a shape setting process). Overlapping portions of the shaped wire 540 can be cut, as shown in FIG. 25, so as to define opposing ends 502', 504' being positioned adjacent each other. A sleeve 550 (also referred to as a "crimp sleeve"), as shown in FIG. 26, comprising a cylindrical body 551 having opposing open ends 552, 553 can be used to join the opposing ends 502', 504', as shown in FIG. 27.

For example, in some instances, the body 551 defines an opening 554 extending between the ends 552, 553. As shown in FIG. 27, the opposing ends 502', 504' can be positioned within respective ends 552, 553 of the sleeve 550, and the body 551 can be sufficiently crimped adjacent the ends 552', 553' such that the sleeve engages the shaped wire 540 ends 502', 504' of the wire at locations 552', 553' and forms a completed wireform frame 560 of the type shown in FIG. 8.

Leaflets

With reference to FIGS. 28 and 29, leaflets 300 as disclosed herein and being compatible with the disclosed valve 100 (FIGS. 5A and 5B), e.g., allowing the commissure tips 235 to extend radially outward of the sewing ring 260, will be described by way of comparison to a leaflet 50 of a conventional prosthetic valve (not shown). In alternative embodiments, the valve 100 can include conventional leaflets 50, but they can restrict movement of the commissure tips 235 and/or can be subject to undesirable stresses during the cardiac cycle.

The leaflet 300 shown in FIG. 29 comprises a leaflet body 301 and opposing, outwardly extending leaflet tabs 303 positioned on opposite sides of the leaflet body. The body 301 and tabs 303 collectively define an outlet periphery 304 (e.g., an edge) extending from an outermost corner of one tab, across the one tab, the body and the other tab, to an outermost corner of the other tab. The leaflet 300 also defines opposing regions 312a, 312b that can contact corresponding regions of an adjacent leaflet when the leaflets coapt under a negative pressure gradient, as described above. The opposing regions 312a, 312b are bounded by respective inlet boundaries 307a, 307b separating the region of the leaflet body 301 that does not contact an adjacent leaflet and the regions 312a, 312b that contact corresponding regions of an adjacent leaflet.

The outlet periphery 304 defines a first, lowermost region 310, opposing second, intermediate regions 308a, 308b, and opposing third, uppermost regions 313a, 313b. The opposing third regions 313a, 313b extend to the respective regions 306a, 306b where the body periphery joins the corresponding tabs 303. Each of the first, second and third regions has a corresponding radius-of-curvature that, together, at least partially define an outer contour of the body 301. The first region 310 and the third regions 313a, 313b are separated by the second regions 308a, 308b. The second regions 308a, 308b are separated from the respective adjacent third regions 313a, 313b at (or near) the point where the boundaries 307a, 307b intersect the outer periphery of the valve body 301.

As shown in FIG. 28, the respective radii-of-curvature of the first region 310 (extending from about point B to about point C on the outer periphery 304) and the third regions 313a, 313b (extending from about point A to corner 306a of the adjacent tab 303 and from about point D to corner 306b of the adjacent tab 303) are greater than the radius-of-curvature of either of the second regions 308a, 308b (extending from about point A to about point B and from about point C to about point D, respectively). The just-described body contour provides a leaflet body 301 that can allow an outlet end 104 of a valve 100 (FIGS. 5A and 5B) to open more widely and/or to allow disclosed commissure portions of valves to extend radially outward to a larger degree than conventional leaflets would allow, providing, at least in part, valves having the improved hemodynamics discussed above.

More specifically, the broad radius near the cusp and decreasing radius of curvature approaching the commissure region introduces a small amount of slack in the leaflets. The leaflet design, in conjunction with the outwardly leaning commissure posts 201, allow the leaflets to provide a relatively larger outlet opening for blood during systole, which reduces the pressure gradient across the valve during systole.

Leaflets as disclosed herein can be formed using conventional materials, such as natural tissue (e.g., bovine, porcine, cadaver) or biocompatible synthetic materials.

Leaflet and Frame Assembly

As briefly discussed above in connection with FIGS. 5A and 5B, disclosed valves 100 can comprise a cloth-covered frame assembly 200 and three leaflets 300 coupled to the frame assembly. Assembly of a cloth-covered frame assembly 220 will now be described with reference to FIGS. 30 and 31.

FIG. 30 shows the frame 230 shown in FIG. 8 partially covered by a cloth frame cover 245. Opposing ends of a strip of cloth 245 have been brought together to form a butt joint 247. Adjacent the butt joint 247, opposing longitudinal edges 248, 249 of the cloth 245 have been wrapped around a cusp portion 232 of the frame 230 and brought into opposing alignment with each other to form a seam 246 with the opposing edges. The seam 246 can be completed by suturing, or other well known cloth-edge joining techniques. The cloth 245 can be wrapped around the entire elongate frame 230 as just described to arrive at the cloth-covered wire frame portion 220 shown in FIG. 31. Cloth covers can be formed of any biocompatible fabric, such as, for example, polyethylene terephthalate. Other covering techniques are disclosed in U.S. Pat. No. 7,473,275, which is incorporated herein in its entirety.

Similar to the bare wireform frame 230, the cloth-covered wireform frame 220 comprises cusp regions 222 separated by commissure portions 223. Each commissure portion comprises cloth-covered commissure posts 224 extending from respective proximal ends adjacent respective cusps to respective distal ends joined to each other by an arcuate commissure tip 225.

With reference to FIG. 32, a sub-assembly 350 comprising a cloth-covered frame portion 220 and three leaflets 300 will be described. In the sub-assembly 350, three leaflets 300 as described above are positioned adjacent to each other in a tricuspid configuration. For example, opposing tabs 320, 321 of two leaflets 300 are positioned in opposing alignment. Stated differently, a portion of an interior surface 315 (e.g., a region near the tab 321) opposes a corresponding interior surface (not shown) of the adjacent, opposing tab 320. As shown in FIG. 33, the opposing pair of tabs 320, 321 is positioned between an opposing pair of commissure posts 224 such that the respective outlet edges of the leaflets are positioned adjacent the arcuate commissure tip 225 of the covered frame 220. Each of the other pairs of tabs 322, 323 and 324, 325 is similarly positioned relative to each other and a respective commissure tip 225.

An outer peripheral portion of the body 301 of each leaflet 300 can be sutured to the cloth cover 245 such that the cloth covered frame 220 supports each leaflet in the tricuspid configuration, shown in FIGS. 26, 27 and 28. For example, the portion adjacent the first region 310 of the periphery can be attached to the cover 245 adjacent the cusp 232 of the covered wireform frame 230 (FIG. 8). This configuration of leaflets provides a closed, fluid occluding surface when exposed to negative pressure gradients (e.g., during systole), and separates to form an open, unobstructed aperture when exposed to positive pressure gradients (e.g., during diastole), as shown in FIGS. 6A and 6B.

Lower Stent/Frame

Referring to FIG. 36, a lower stent, or frame, 270 as disclosed herein is shown in a neutral position 270A and will be described. The illustrated stent 270 defines an interior, substantially cylindrical volume 271 defining a longitudinal axis 272 of the stent. The stent comprises a circumferentially extending base member 273. As shown, some base members can define longitudinally displaced undulations 274 relative to, and positioned between, adjacent cusps 275. Each of a plurality of posts 276 extends longitudinally from a proximal end 277 adjacent a respective undulation 274 to a distal end 278 defining a post tip 279. In some instances, such a stent can be formed from any flexible biocompatible polymer, such as, for example, polypropylene. In another implementation, the stent 270 can be made of silicon with or without a cloth core.

The primary functions of the stent 270 are to provide additional support structure for supporting the leaflets in the triscuspid configuration under working conditions and to provide a structure to which the sewing ring can be attached. The stent is also sufficiently flexible to allow the valve to be longitudinally and/or radially collapsed to a smaller configuration for delivery.

Similar to the wireform 230, the stent 270 can undergo high levels of strain without suffering plastic deformation or other damage. For example, FIGS. 37 and 38 illustrate isometric and side elevation views, respectively, of the stent 270 in a longitudinally collapsed position 270B. In the illustrated position, each of the post tips 278 have been folded radially inward from their respective neutral positions 270A (FIG. 36) and toward the longitudinal axis 272 of the stent. Similar to the wireform frame 230 in its longitudinally collapsed position 239 (FIG. 9), the longitudinally collapsed position 270B of the stent 270 forms a substantially conically shaped interior volume 271', as shown in FIGS. 37 and 38. Although not illustrated, the stent 270 can be radially collapsed in a manner similar to the wireform frame 230, as shown in FIGS. 11 and 13.

Figure 45:
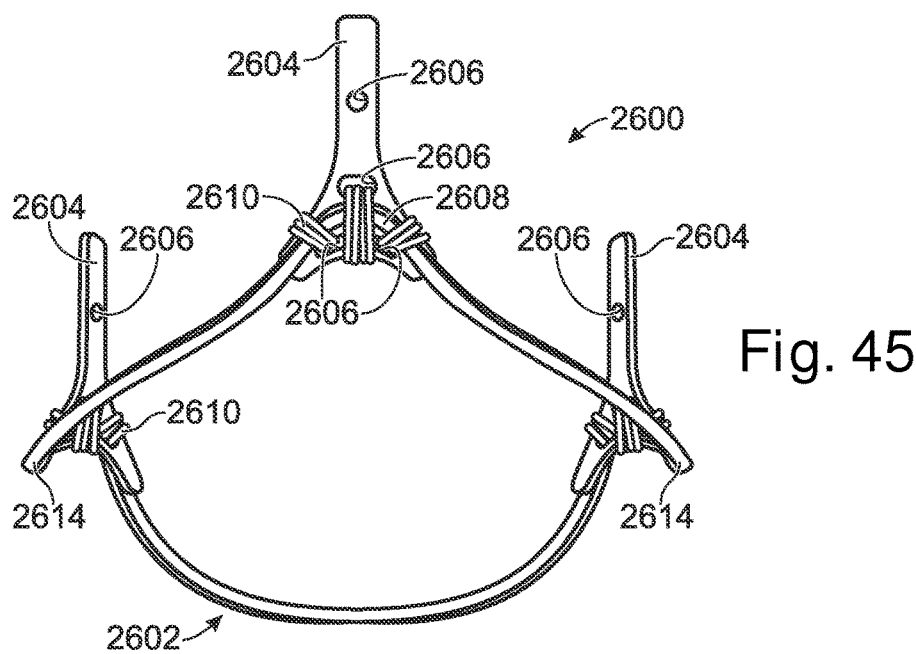
FIG. 45 shows a perspective view of another embodiment of a leaflet support stent for use with the disclosed prosthetic heart valve frame.
Figure 46:
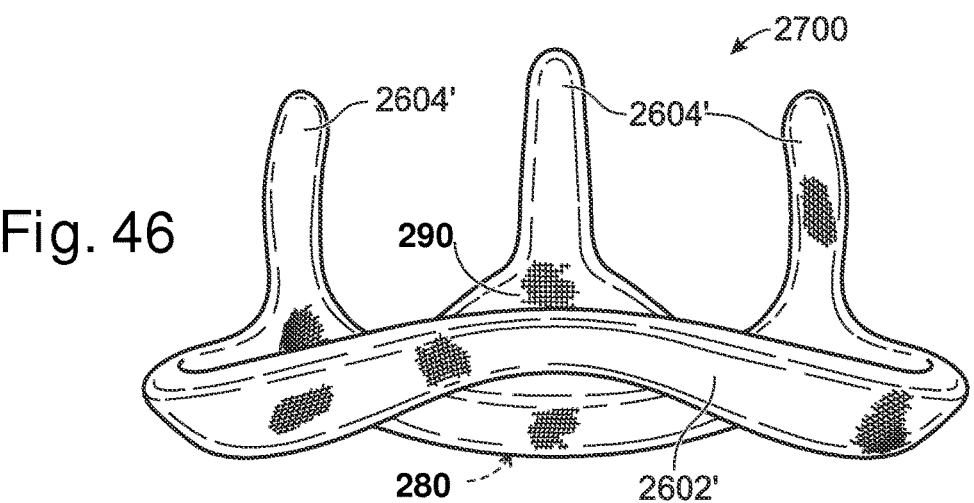
FIG. 46 shows a side elevation view of the leaflet support stent shown in FIG. 45, combined with a sealing ring and having a cloth covering surrounding it.
Figure 47:
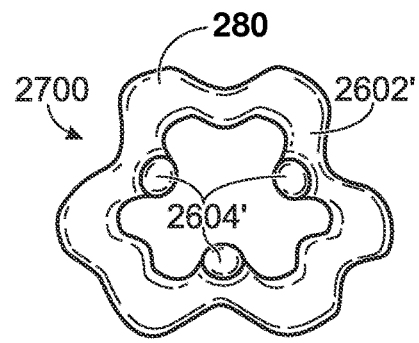
FIG. 47 shows a top plan view of the cloth-covered leaflet support stent of FIG. 46, in a radially compressed configuration.

FIGS. 45-47 illustrate another embodiment of a collapsible stent 2600 that can be used in place of stent 270. FIG. 45 shows a leaflet support stent 2600 that includes a stent frame 2602 and a plurality of commissure tips 2604. The stent frame 2602 can be, for example, a flexible (e.g., radially compressible) stent frame comprising, for example, Nitinol or other superelastic material. The commissure tips 2604 can comprise, for example, a biocompatible polymer such as a polyester.

The stent frame 2602 can be shaped to include three cusp support portions 2614 and three commissure portions 2608 spaced apart from one another, with a commissure portion 2608 positioned between each pair of adjacent cusp portions 2614. A commissure tip 2604 can be secured to each of the commissure portions 2608 of the stent frame 2602. For example, the commissure tips 2604 can each include one or more sewing holes 2606 through which sutures 2610 can be passed and then wrapped around the respective commissure portion 2608, thereby securing each commissure tip to each respective commissure portion 2608. Other suitable means of attachment can also be used.

The leaflet support stent 2600 can have a reduced thickness as compared to other collapsible stents. For example, some embodiments of the leaflet support stent 2600 can be configured to have at least about a 1 mm lower profile than the stent 270 described above. In some embodiments, while the stent 270 may have a thickness of around 1.5 mm, some embodiments of a leaflet support stent 2600 can allow for a reduced thickness of around 0.5 mm. For example, the leaflet support stent 2600 can be formed from a wire having a thickness of around 0.5 mm. When the valve portion of a prosthetic heart valve is positioned on top of the leaflet support stent 2600, the overall height of the prosthetic valve can therefore be reduced by around 1 mm as compared to the height of the overall prosthetic valve that includes the stent 270.

While the commissure tips 2604 are shown positioned on the inside of the stent frame 2602, they can alternatively be positioned on the outside of the stent frame 2602. In alternative embodiments, similar commissure tips can be configured to be positioned on top of the commissure portions 2608, and thus neither inside nor outside the stent frame 2602. In some embodiments, the commissure tips can be formed integrally with the stent frame. The commissure tips 2604 can be secured to the stent frame 2602 such that the commissure tips 2604 are substantially prevented from moving in the axial direction with respect to the stent frame 2602. However, the coupling of the commissure tips 2604 to the commissure portions 2608 can be configured so as not to interfere with the radial collapsibility of the overall leaflet support stent 2600.

The leaflet support stent 2600 can be combined with a sealing ring (e.g., sealing ring 280 shown in FIG. 39) and covered in cloth 290 as described above to form a collapsible stent subassembly 2700, seen in FIG. 46. As shown in FIG. 46, the cloth-covered stent frame 2602', the cloth-covered commissure tips 2604', and the cloth-covered sealing ring 280 form the collapsible stent subassembly 2700.

FIG. 47 shows the subassembly 2700 in a radially collapsed configuration. Some embodiments of the subassembly 2700 can be radially compressed to a relatively smaller diameter than the collapsible stent of FIGS. 36-38, as shown, and return to its expanded, unstressed configuration shown in FIG. 46 when any external crimping restraint is removed. When the subassembly 2700 is radially compressed, the cloth-covered commissure posts 2604' can remain substantially vertical (e.g., substantially parallel to the axial direction of the leaflet support stent) such that they do not interfere with the radial compressibility of the subassembly 2700. Additional details concerning embodiments of a collapsible leaflet support stent 2600 are disclosed in U.S. Patent Application No. 61/472,083, which is incorporated herein by reference.

Sewing Ring Insert

With reference to FIGS. 39 and 40, an example of a sewing ring insert 280 will now be described. The body 281 of the illustrated sewing ring insert 280 comprises a frusto-conical, annular body-of-rotation. In other words, the illustrated body 281 defines a body of rotation about a sewing ring axis 282 extending longitudinally of the body. The body 281 defines a major circumference 283 having a major diameter D and a minor circumference 284 having a minor diameter d, and a tapering wall 285 extending between the major circumference and the minor circumference. The wall 285 can have a relatively smooth (i.e., untextured) inner surface 286. The wall can have an outer surface 287 that is roughened, or provided with retention features (e.g., ridges, including barbs 288, as shown in FIGS. 39 and 40).

As described more fully below in context of the prosthetic valve assembly 100, the illustrated ridges formed by the outer surface 287 can provide the sewing ring portion 260 with an uneven outer contour that can engage the surrounding tissue of the implantation site. Such engagement can provide the prosthetic valve with improved purchase at the implantation site (e.g., as compared to only suturing the valve).

For example, the taper of the wall 285 can facilitate placement at a desired implantation site as the minor diameter first comes into contact with the surrounding tissue of the lumen. As the sewing ring is urged longitudinally into the lumen, the tissue can expand and slide longitudinally of the outer surface 287. The barbs or other retention features 288 can engage the surrounding tissue and at least partially retain the sewing ring within the surrounding lumen until the sewing ring can be permanently secured in place, as by suturing.

In addition, such ridges can stiffen the sewing ring insert 280, adding to the resiliency of the sewing ring portion 260. Even so, the sewing ring 260 preferably is flexible for allowing the valve 100 to collapse (e.g., radially collapse). In some embodiments, the sewing ring insert 280 comprises a silicone-based material, although other suture-permeable materials can be used. Other sewing ring inserts 280 can comprise a relatively stiff, or even a rigid, material. In such embodiments, the extent to which the valve can be radially collapsed may be limited, but the cantilevered commissure portions can still be folded inwardly to longitudinally collapse the valve for delivery.

Stent and Sewing Ring Sub-Assembly

Assembly of the stent and sewing ring sub-assembly will now be described in connection with FIGS. 7 and 34.

Referring to FIG. 41, a tubular (e.g., cylindrically tubular) stent covering cloth 290 is shown axially aligned with the stent 270 and the sewing ring insert 280. In other words, the longitudinal axis of the covering cloth 290 is co-axially aligned with the respective longitudinal axes 272, 282 of the stent 270 and the sewing ring 280. The covering cloth 290 can comprise any suitable biocompatible fabric.

The whole of the stent 270 can be inserted into the interior of the tubular cloth 290. The sewing ring insert 280 can also be inserted into the interior of the tubular cloth 290. As best shown in FIG. 7, the sewing ring insert and the stent can be co-centrically positioned with respect to each other such that the insert 280 circumscribes the base 273 and the minor circumference 284 of the insert is aligned with the lower edge of the base 273 of the stent 270.

The tubular cloth has a length L extending between its respective open ends 291 and measuring more than about twice the length 1 of the stent 270 (measured from a cusp portion 275 to a post tip 278 (FIG. 36). Once the stent 270 and the sewing ring insert 280 have been positioned within the tubular cloth 290, a free end portion 292 of the cloth can be folded inwardly on itself. In other words, a "top" edge 293 corresponding to the free end portion 292 can be rolled inwardly toward the tube's interior and pulled through the cylindrical interior 271 of the stent 270 (FIG. 36), so as to line both the interior and exterior surfaces of the stent with the cloth 290 and to juxtapose the opposing ends 291 of the tubular cloth.

Referring to the cross-section shown in FIG. 7, the juxtaposed ends 291 can overlap, as shown by the overlapping cloth 294 adjacent the barbs of the sewing ring insert 280. Excess cloth adjacent the cusps 273 and/or posts can be rolled to form the roll 292. In some instances, such seams are sutured.

In other embodiments, a leaflet support stent 2600 (FIG. 45) can be used in place of stent 270 as described above, with the sewing ring insert 280 and cloth covering 290 coupled to the leaflet support stent 2600 instead of collapsible stent 270.

Final Assembly of a Prosthetic Valve

As shown in FIG. 5B, the stent and sewing ring subassembly 250 as just described and illustrated can be coupled to the subassembly comprising the wireform portion 220 and corresponding leaflets 300, to assemble the valve 100.

As shown in the exploded view of FIG. 5B, the subassembly 250 can matingly engage a corresponding contour of the covered wireform 220. In other words, as shown, for example, in FIG. 5B, the covered posts 256 of the assembly 250 can be so sized and shaped as to overlie, or be inserted within, corresponding commissure portions 353 of the wireform 230 and leaflet assembly 350. Once in position, the cloth covering of the posts 256 and stent can be sutured to the cloth covering of the wireform 220, so as to substantially complete the prosthetic valve assembly 100. In addition, if desired, covers 295 can be positioned over the exposed portions of the commissure tabs of the leaflets, and secured in place with sutures 296 (FIG. 5B). The covers can be formed of any suitable biocompatible fabric.

Delivery Systems

Figure 43:
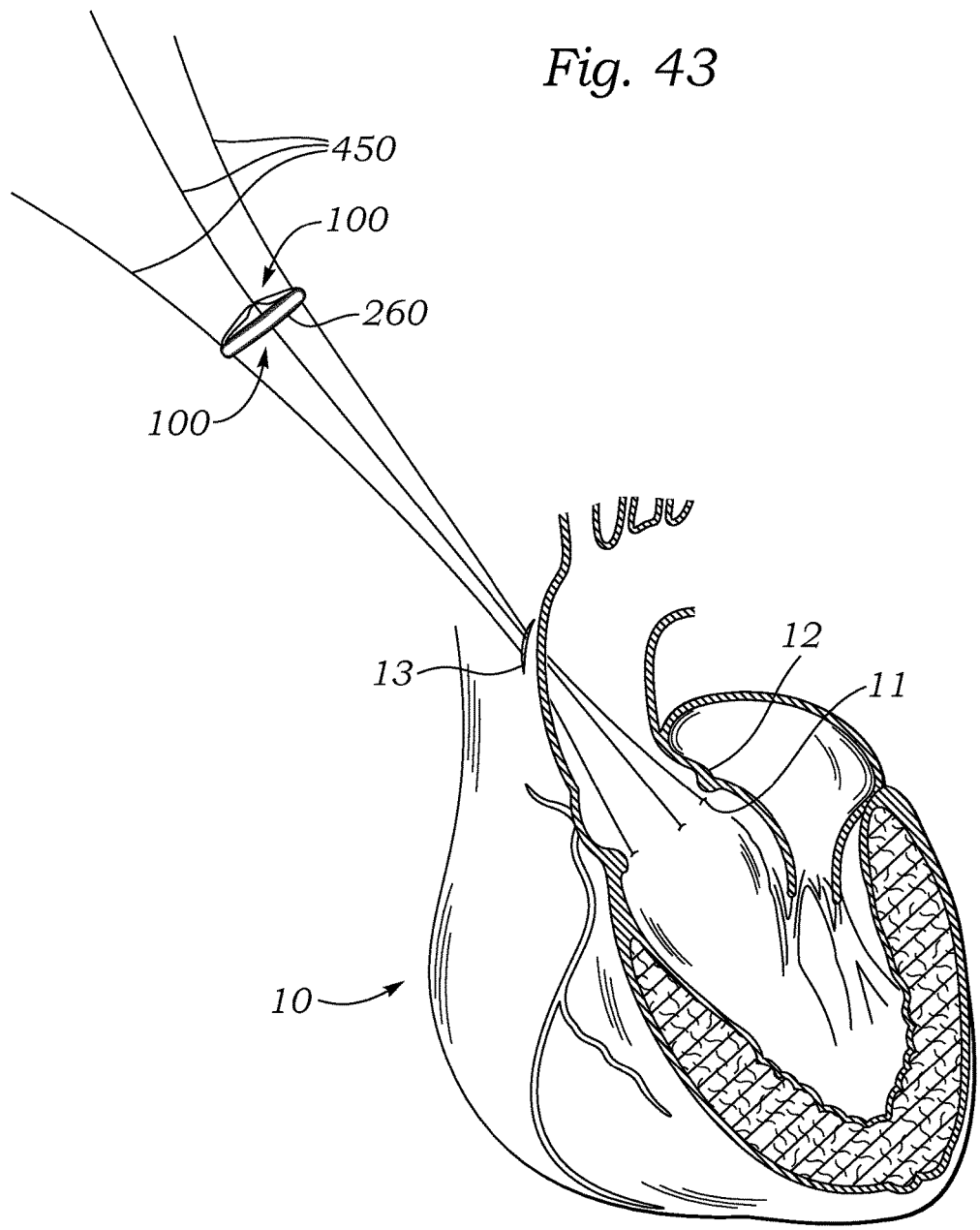
FIG. 43 shows a valve as disclosed herein in a collapsed delivery configuration and being delivered to, for example, the aortic annulus using a "parachuting" delivery technique.

Examples of delivery systems for disclosed prosthetic valves will now be described. Valves as described herein can be delivered to the implantation site manually, or with the assistance of a manually-controlled instrument 600 (FIGS. 42A-42D) and/or one or more sutures 450 (FIG. 43).

In some embodiments, access to the sewing ring 260 can be at least partially obstructed by one or more portions of the valve 100 (e.g., longitudinally extending commissure portions 201). For such embodiments, it may be convenient to longitudinally collapse the valve 100 to, and to retain the valve in, a longitudinally collapsed delivery position (e.g., the frame 230 is shown in such a configuration in FIG. 9).

By way of example, a suture can couple the commissure tips 202 (FIG. 5A) to each other, or to another portion of the valve, such as a cusp portion of the frame, so as to maintain the collapsed position 239 (FIG. 9) and to prevent the frame from self-expanding to the neutral position 238.

A longitudinally collapsed valve can, in some embodiments, also be radially collapsed (e.g., FIG. 11) to aid insertion of the collapsed valve through a relatively small incision (e.g., using a "shoe-horning" technique, as described more fully below). One or more sutures can be used to retain the valve in a radially collapsed position.

In some delivery systems, a single suture can be used to retain the valve in the longitudinally and the radially collapsed positions just described. In such a system, cutting the suture allows the valve to self-expand to its original neutral position (and/or to an implanted neutral configuration). In other delivery systems, one or more sutures used to retain the valve in the longitudinally collapsed position are independent of the one or more sutures used to retain the valve in the radially collapsed configuration. In this approach, the valve 100 can remain longitudinally collapsed upon releasing the valve from the radially collapsed position. This can be useful, for example, during implantation, since the radially collapsed valve can be more easily inserted through an incision in the lumen, and a radially expanded valve can be more easily secured in the lumen, particularly when the valve remains longitudinally collapsed such that the cantilevered commissure portions do not interfere with access to the securing portion of the valve (e.g., the sewing ring). Once the longitudinally collapsed valve has been adequately secured within the lumen, the valve can be released from its longitudinally collapsed position and allowed to self-expand to the implanted neutral configuration.

As noted above, a manually-controlled instrument, or delivery device 600 (FIGS. 42A-42D), can be used to assist delivery of disclosed valves to an implantation site. For example, as shown in FIG. 42D, the illustrated instrument 600 comprises a handle 610 and optional actuators (not shown) at a proximal end of the instrument and a valve holder 630 at a distal end of the instrument.

The holder 630 can be configured to secure a valve 100 to the instrument and/or to retain the valve in a collapsed deployment configuration (e.g., a radially collapsed configuration and/or a longitudinally collapsed configuration). In other words, a valve retained in its collapsed configuration (e.g., by sutures) can be held by the holder 630. In particular embodiments, the instrument is configured to selectively retain and release a valve from a radially and/or longitudinally collapsed configuration by actuation of various actuators on the handle 610.

A shaft 620, which can be flexible and/or deformable, extends between the handle 610 and the holder 630. The holder 630 in the illustrated embodiment comprises a central hub 634 and a plurality of angularly spaced leg portions 632a, 632b, 632c extending from the hub 634. The leg portions 632a, 632b, 632c are positioned relative to the commissure posts 201 of the valve 100 such that each leg portion is aligned behind and bear against a respective commissure post so as to retain the commissure post in a longitudinally collapsed position (as best shown in FIG. 42B). In contrast, the most common way of delivering a surgical valve involves securing the leg portions of a valve holder between two adjacent commissure posts of the valve. In any case, as best shown in FIG. 42A, the leg portions 632a, 632b, 632c can be releasably secured to the commissure posts, such as with a suture or wire 636 that is threaded through apertures in the holder and through the sewing ring 260 at the base of each commissure post. The leg portions retain the commissure posts in the longitudinally collapsed position during delivery and suturing of the valve to a native annulus and can be released from the longitudinally collapsed position by manually cutting and removing the suture 636 or actuating an actuator on the handle 610 that automatically causes the leg portions to release the commissure posts.

As shown in FIG. 42C, the valve can also be retained in a radially collapsed configuration, such as by employing another suture or wire 638 that is threaded through opposing locations on the sewing ring 260 and pulled taught to cause the sewing ring to collapse radially. In this radially collapsed position, the valve appears to be pinched on opposite sides of the sewing ring. The suture 638 can be tied off to a convenient location on one of the leg portions of the valve holder as shown. The valve can be released from the radially collapsed configuration after delivery to the implantation site by manually cutting and removing the suture 638 or actuating an actuator (e.g., a lever or trigger) on the handle 610 that automatically releases tension on suture 638, which in turn allows the sewing ring to self-expand back to its functional size. Such an actuator can be configured to apply and release tension on suture 638 so as to collapse and expand the valve, respectively, as needed by the operator.

In certain embodiments, the shaft 620 can be hollow so as to convey one or more linkages coupling the actuators and the holder. Such linkages can activate the holder 630 (e.g., retain the valve in a collapsed position, release the valve from a collapsed position and/or pivot the holder relative to the shaft) by actuation of various actuators on the handle. Some delivery instruments 600 comprise an articulatable joint (not shown) between the holder 630 and the shaft 620. Such a joint, when activated, can assist the operator in performing a shoehorning insertion technique.

As noted above, the collapsed valve can be introduced to a body lumen using the "shoehorning" technique. Referring to FIG. 43 for example, an under-sized incision 13 (relative to a cross-sectional dimension of the valve 100 in its neutral position) can be made in the lumen wall (e.g., the descending aorta). The collapsed valve (e.g., radially and/or longitudinally collapsed) can be inserted through the incision at an angle relative to a plane defined by the incision, much like passing a button through a button-hole. After insertion through the incision, the valve can be released from its radially collapsed position, and the sewing ring 260 can be secured to the implantation site 11. As noted above, the commissure portions of the valve are desirably retained in a longitudinally collapsed configuration during suturing for increased access to the sewing ring. After being secured, the valve can be released from its longitudinally collapsed configuration and allowed to self-expand to the implanted neutral configuration.

As mentioned above, a disclosed valve 100 can be implanted in a body lumen with the assistance of the delivery instrument 600. To implant a valve using the instrument 600, a surgeon can open an outer incision (e.g., in the patient's thorax), and a second, incision in the lumen in which the valve is to be implanted (e.g., an aortotomy 13 (FIG. 43)). The valve 100 can be mounted to the holder 630 and placed in a radially and longitudinally collapsed state as depicted in FIG. 42C. The holder and collapsed valve can be inserted through the outer incision, and the shaft 620 can extend to the opened lumen, placing the collapsed valve adjacent the second incision. With some delivery devices, actuators in the handle can be actuated to articulate the holder 630 to avoid anatomy as the holder 630 passes through the patient's thorax, and/or through the lumen incision. After the valve is passed through the incision in the lumen, the valve can be released from the radially collapsed position, such as by cutting or releasing tension in suture 638, and then positioned against the native annulus (e.g., the aortic annulus 12). The valve can then be secured in place by suturing the sewing ring 260 to the native annulus, after which the valve can be released from the longitudinally collapsed state, such as by cutting suture 636 to release the holder 630 from the valve. Retracting the holder 630 away from the valve allows the commissure posts 201 to self-expand to an implanted neutral configuration.

As shown in FIG. 43, and to assist in the delivery of a collapsed valve to the implantation site (e.g., the aortic annulus), an array of implant sutures 450 can be secured around the periphery 11 of the native annulus 12, and the opposite ends of the sutures can be pulled through the incision 13 and threaded through the sewing ring 260 of the prosthetic valve 100. The prosthetic valve can be "parachuted" down the array of sutures until the valve rests against the native annulus, and the sutures 450 can be tied off to secure the prosthetic valve to the annulus. This "parachuting approach" can be used independently of, or in combination with, the delivery instrument 600. In any case, after the valve is passed through the incision 13 and before it is secured to the annulus 12, the valve can be released from a radially collapsed state as described above. Once the valve is sutured to the annulus 12, the valve 100 can be released from the longitudinally collapsed state (and/or from the delivery apparatus 600), the delivery apparatus is removed from the body and the incisions in the lumen and thorax can be closed.

In alternative embodiments, the valve 100 can be implanted within the heart using any known techniques. For example, the valve 100 can be delivered and implanted using a conventional valve holder that does not retain the valve in a collapsed delivery configuration (either a radially or longitudinally collapsed configuration).

Example

Figure 44:
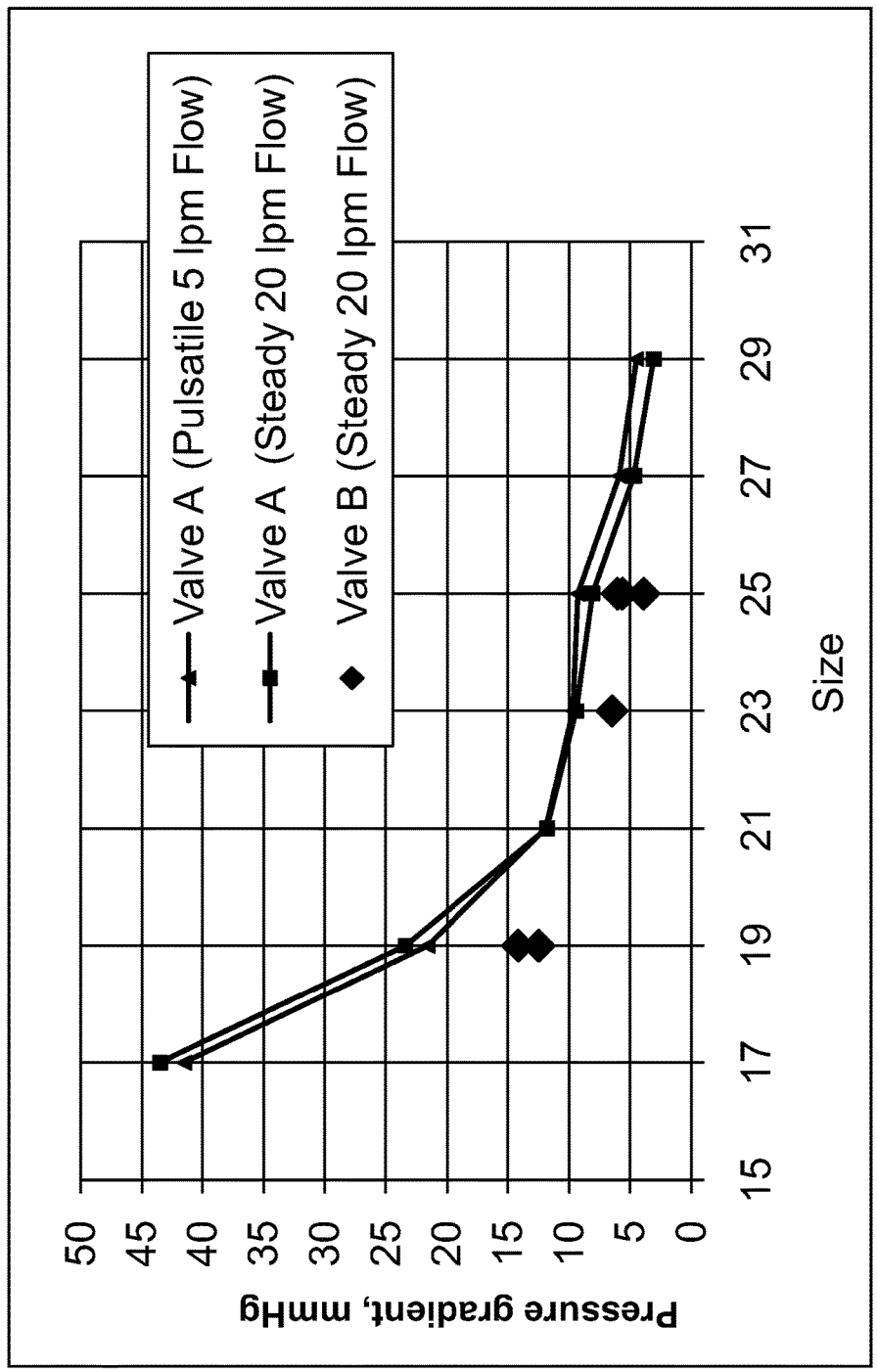
FIG. 44 is a graph illustrating the pressure gradient measured across valves having a conventional leaflet and frame design and valves having a modified leaflet and frame design according to the present disclosure.

Multiple valves 100 were constructed in nominal sizes of 19 mm, 23 mm, and 25 mm. The valves 100 were placed in a testing apparatus and subjected to a 20 lpm steady-state flow. FIG. 44 shows the pressure gradient measured across the valves 100 (identified as "Valve B" in FIG. 44) and the pressure gradient measured across various sizes of a known valve (identified as "Valve A") at a 20 lpm steady-state flow and a 5 lpm pulsatile flow. The valve A configuration had a conventional leaflet configuration (leaflet 50 in FIG. 28) and a rigid frame having commissure posts extending substantially perpendicularly to the sewing ring. As can be seen in FIG. 44, valve B experienced a lower pressure drop than valve A at all three sizes of valve B.

Other Embodiments

Many embodiments of prosthetic valves and delivery systems being compatible with minimally invasive surgical techniques are possible by incorporating one or more of the principles described above. This disclosure makes reference to the accompanying drawings which form a part hereof, wherein like numerals designate like parts throughout. The drawings illustrate features of specific embodiments, but other embodiments may be formed and structural changes may be made without departing from the intended scope of this disclosure.

Directions and references (e.g., up, down, top, bottom, left, right, rearward, forward, etc.) may be used to facilitate discussion of the drawings but are not intended to be limiting. For example, certain terms have been used such as "up", "down", "upper", "lower", "horizontal", "vertical", "left", "right", and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and", as well as "and" and "or."

Accordingly, this detailed description shall not be construed in a limiting sense, and following a review of this disclosure, those of ordinary skill in the art will appreciate the wide variety of prosthetic valves that can be devised and constructed using the various concepts described herein. Moreover, those of ordinary skill in the art will appreciate that the exemplary embodiments disclosed herein can be adapted to various configurations without departing from the disclosed concepts. Thus, in view of the many possible embodiments to which the disclosed principles can be applied, it should be recognized that the above-described embodiments are only examples and should not be taken as limiting in scope. Therefore, we claim all that comes within the scope and spirit of the following claims.

We claim:

1. A prosthetic-valve delivery system comprising:
   a prosthetic valve being collapsible and expandable between a collapsed delivery configuration and a neutral configuration, the valve comprising a sewing ring configured to be secured to an implantation site, and a resilient frame configured to cause the valve to expand from the collapsed delivery configuration to the neutral configuration, wherein the prosthetic valve further comprises a plurality of cantilevered commissure posts extending substantially longitudinally of the valve and being cantilevered relative to the sewing ring in the neutral configuration, wherein, in the collapsed deployment configuration, at least a portion of one of the plurality of cantilevered commissure portions is positioned radially inward of the sewing ring, and wherein each of the plurality of commissure posts extends radially outward of the sewing ring in the neutral configuration; and
   a delivery device configured to assist the delivery of the valve to the implantation site when the valve is in the collapsed delivery configuration.

2. The delivery system of claim 1, wherein the delivery device comprises an elongate configuration having a handle at a proximal end and a holder at an opposing distal end, wherein the holder is configured to retain the valve during delivery of the valve to the implantation site.

3. The delivery system of claim 2, wherein the holder is further configured to collapse the valve to the collapsed delivery configuration.

4. The delivery system of claim 3, wherein the collapsed delivery configuration comprises one or both of a longitudinally collapsed configuration and a radially collapsed configuration.

5. The delivery system of claim 2, wherein the delivery device is further configured to release the frame from the collapsed delivery configuration.

6. The delivery system of claim 2, wherein the delivery system comprises one or more actuators being so configured as to cause the holder to release the valve from the collapsed delivery configuration upon actuation of the one or more actuators.

7. The delivery system of claim 6, wherein the delivery device comprises one or more actuators configured to cause the holder to so contract as to collapse the valve to the collapsed delivery configuration.

8. The delivery system of claim 1, wherein the frame comprises a super-elastic alloy.

9. The delivery system of claim 1, wherein the collapsed delivery configuration comprises one or both of a longitudinally collapsed configuration and a radially collapsed configuration.

10. The delivery system of claim 1, wherein the delivery device comprises a handle at a proximal end and a valve holder at an opposing distal end, and the valve holder comprises a central hub and a plurality of angularly spaced leg portions extending therefrom, wherein each leg portion is aligned radially outside of and bears against a respective commissure post so as to retain the commissure post in a longitudinal collapsed position.

11. The delivery system of claim 1, wherein the frame, in the collapsed deployment configuration, is configured to be at least partially collapsed radially.

12. The delivery system of claim 1, wherein, when in the collapsed deployment configuration, the commissure portions are held in place using one or more connecting sutures secured to legs on the valve holder, and the valve is at least partially released from the collapsed delivery configuration by severing the connecting suture(s).

13. The prosthetic-valve delivery system of claim 1, wherein the delivery device comprises a suture configured to at least partially guide the valve to the implantation site during delivery.

14. A method of using the prosthetic-valve delivery system of claim 1, the method comprising:
retaining the prosthetic valve in its collapsed delivery configuration;
making an incision in a body lumen adjacent an implantation site;
inserting the collapsed prosthetic valve through the incision using the delivery device;
securing the sewing ring to surrounding tissue within the body lumen; and
releasing the prosthetic valve from the collapsed delivery configuration such that the valve independently recovers to the neutral configuration within the body lumen.

15. The method of claim 14, further comprising:
securing one or more sutures to tissue adjacent the implantation site and extending the one or more of the sutures outwardly through the incision and through the sewing ring of the prosthetic valve; and
sliding the prosthetic valve along the one or more sutures and through the incision until the prosthetic valve engages the implantation site.

16. The method of claim 14, wherein the valve comprises the plurality of cantilevered commissure portions, and wherein the commissure portions are folded inwardly to a longitudinally collapsed position when the valve is positioned in the collapsed delivery configuration.

17. The method of claim 14, wherein the valve is released from the collapsed delivery configuration after the sewing ring has been secured to the surrounding tissue.

18. The method of claim 14, wherein the valve is at least partially released from the collapsed delivery configuration before the sewing ring has been secured to the surrounding tissue.

19. The method of claim 14, wherein:
the act of retaining the valve in the collapsed delivery configuration comprises longitudinally and radially collapsing the valve;
the act of releasing the valve from the collapsed delivery configuration comprises allowing the valve to radially expand before the sewing ring has been secured to the surrounding tissue;
the act of securing the sewing ring comprises securing the sewing ring to the surrounding tissue after the valve has radially expanded; and
the act of releasing the valve from the collapsed delivery configuration further comprises allowing the valve to expand longitudinally after the sewing ring has been secured to the surrounding tissue.

20. A prosthetic-valve delivery system comprising:
a prosthetic valve being collapsible and expandable between a collapsed delivery configuration and a neutral configuration, the valve comprising a sewing ring configured to be secured to an implantation site, and a resilient frame including convex cusp portions on an inflow end thereof intermediate convex commissure portions on an outflow end thereof, the resilient frame being made from a super elastic alloy to permit the valve to expand from the collapsed delivery configuration to the neutral configuration; and
a delivery device configured to assist the delivery of the valve to the implantation site when the valve is in the collapsed delivery configuration including a valve holder on a distal end of a shaft, wherein the commissure portions of the resilient frame are also folded inwardly to a longitudinally collapsed position when the valve is positioned in the collapsed delivery configuration and held in place with legs on the valve holder wherein, when in the collapsed delivery configuration, the valve is retained in a radially collapsed configuration using a suture or wire threaded through opposing locations around the valve, pulled taught and secured to the valve holder to cause the valve to collapse radially so that the resilient frame defines an oval prism, rather than a cylinder or a circular prism, and the valve is at least partially released from the collapsed delivery configuration by severing the suture or wire.

21. The delivery system of claim 20, wherein the valve holder comprises a central hub and a plurality of angularly spaced leg portions extending therefrom, and wherein each leg portion is aligned radially outside of and bears against a respective commissure post so as to retain the commissure post in the longitudinally collapsed position.

22. The delivery system of claim 20, wherein the legs on the valve holder are secured to the commissure portions of the resilient frame with one or more connecting sutures, and valve is at least partially released from the collapsed delivery configuration by severing the connecting suture(s).

* * * * *